(12) United States Patent
Baker et al.

(10) Patent No.: US 8,617,449 B2
(45) Date of Patent: Dec. 31, 2013

(54) METHOD OF MAKING AN ABSORBENT STRUCTURE HAVING THREE-DIMENSIONAL TOPOGRAPHY

(75) Inventors: Andrew Thomas Baker, Norcross, GA (US); Theresa Michelle McCoy, Cumming, GA (US); Stephen Avedis Baratian, Roswell, GA (US); Charles Wilson Colman, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/479,610

(22) Filed: May 24, 2012

(65) Prior Publication Data
US 2012/0232514 A1    Sep. 13, 2012

Related U.S. Application Data

(63) Continuation of application No. 10/460,882, filed on Jun. 13, 2003, now Pat. No. 8,211,815.

(51) Int. Cl.
    *B29C 43/02*    (2006.01)
    *B29C 43/24*    (2006.01)
    *B29C 67/20*    (2006.01)
    *A61F 13/15*    (2006.01)

(52) U.S. Cl.
    USPC ....... 264/321; 264/175; 264/319; 604/385.01

(58) Field of Classification Search
    None
    See application file for complete search history.

(56) References Cited

U.S. PATENT DOCUMENTS

| | | |
|---|---|---|
| 3,046,986 A | 7/1963 | Harwood |
| 3,338,992 A | 8/1967 | Kinney |
| 3,341,394 A | 9/1967 | Kinney |
| 3,375,827 A | 4/1968 | Bletzinger et al. |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,881,490 A | 5/1975 | Whitehead et al. |
| 3,929,135 A | 12/1975 | Thompson |
| 3,971,373 A | 7/1976 | Braun |
| 4,027,672 A | 6/1977 | Karami |
| 4,079,739 A | 3/1978 | Whitehead |

(Continued)

FOREIGN PATENT DOCUMENTS

| | | |
|---|---|---|
| DE | 4321155 A1 | 1/1995 |
| EP | 0518340 A1 | 12/1992 |
| EP | 1236827 A1 | 9/2002 |
| WO | 0126595 A1 | 4/2001 |

OTHER PUBLICATIONS

International Search Report for PCT/US2004/006007 dated Dec. 13, 2005; 5 pages.

*Primary Examiner* — Christina Johnson
*Assistant Examiner* — Benjamin Schiffman
(74) *Attorney, Agent, or Firm* — Armstrong Teasdale LLP

(57) ABSTRACT

A method of making an absorbent structure having a three-dimensional topography includes placing at least a portion of the absorbent structure between opposed mold surfaces. At least one of the mold surfaces has a three-dimensional topography. The three-dimensional topography of the mold surface is imparted onto the absorbent structure so that the absorbent structure has a three-dimensional topography corresponding to the three-dimensional topography of the mold surface.

15 Claims, 22 Drawing Sheets

(56) References Cited

U.S. PATENT DOCUMENTS

| | | |
|---|---|---|
| 4,100,324 A | 7/1978 | Anderson et al. |
| 4,264,289 A | 4/1981 | Day |
| 4,333,979 A | 6/1982 | Sciaraffa et al. |
| 4,340,563 A | 7/1982 | Appel et al. |
| 4,341,217 A | 7/1982 | Ferguson et al. |
| 4,351,793 A | 9/1982 | Day |
| 4,443,512 A | 4/1984 | Delvaux |
| 4,494,278 A | 1/1985 | Kroyer et al. |
| 4,640,810 A | 2/1987 | Laursen et al. |
| 4,670,011 A | 6/1987 | Mesek |
| 4,795,668 A | 1/1989 | Krueger et al. |
| 4,834,735 A | 5/1989 | Alemany et al. |
| 5,069,676 A | 12/1991 | Ito et al. |
| 5,108,820 A | 4/1992 | Kaneko et al. |
| 5,128,193 A | 7/1992 | Anapol et al. |
| 5,147,343 A | 9/1992 | Kellenberger |
| 5,242,435 A | 9/1993 | Murji et al. |
| 5,336,552 A | 8/1994 | Strack et al. |
| 5,350,624 A | 9/1994 | Georger et al. |
| 5,368,910 A | 11/1994 | Langdon |
| 5,382,400 A | 1/1995 | Pike et al. |
| 5,540,872 A | 7/1996 | Ulman |
| 5,540,992 A | 7/1996 | Marcher et al. |
| 5,547,747 A | 8/1996 | Trokhan et al. |
| 5,578,024 A | 11/1996 | Mizutani et al. |
| 5,613,960 A | 3/1997 | Mizutani |
| 5,669,895 A | 9/1997 | Murakami et al. |
| 5,883,231 A | 3/1999 | Achter et al. |
| 5,948,710 A | 9/1999 | Pomplun et al. |
| 5,990,377 A | 11/1999 | Chen et al. |
| 6,037,518 A | 3/2000 | Guidotti et al. |
| 6,093,665 A | 7/2000 | Sayovitz et al. |
| 6,129,717 A | 10/2000 | Fujioka et al. |
| 6,332,996 B1 | 12/2001 | Dit Picard et al. |
| 6,362,391 B1 | 3/2002 | Mizutani et al. |
| 6,375,644 B2 | 4/2002 | Mizutani |
| 6,410,823 B1 | 6/2002 | Daley et al. |
| 6,417,427 B1 | 7/2002 | Roxendal et al. |
| 6,441,268 B1 | 8/2002 | Edwardsson |
| 6,447,494 B1 | 9/2002 | Kashiwagi et al. |
| 6,468,626 B1 | 10/2002 | Takai et al. |
| 6,488,670 B1 | 12/2002 | Schild et al. |
| 6,503,598 B1 | 1/2003 | Goda et al. |
| 7,105,716 B2 * | 9/2006 | Baratian et al. ............... 604/367 |
| 2003/0014028 A1 | 1/2003 | Colman et al. |
| 2003/0203691 A1 * | 10/2003 | Fenwick et al. ............... 442/327 |

* cited by examiner

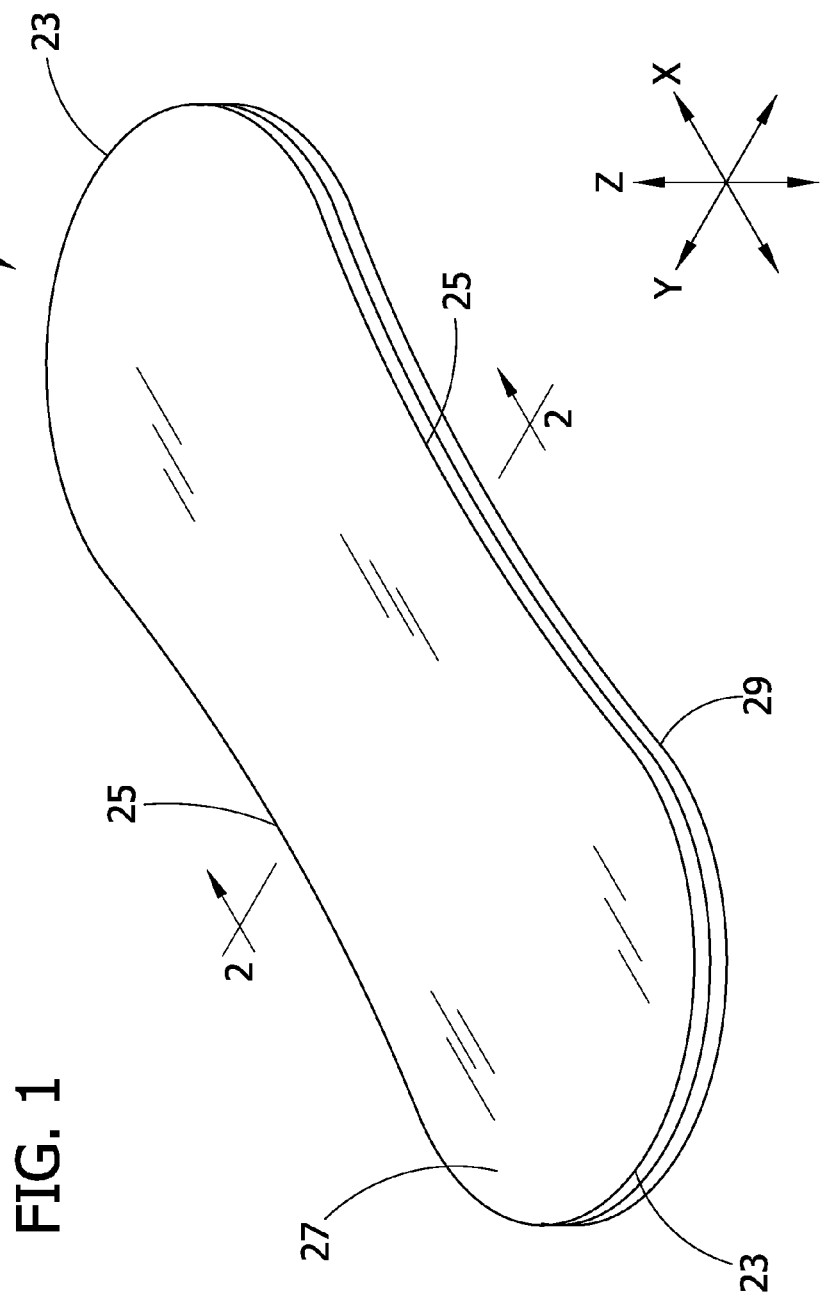

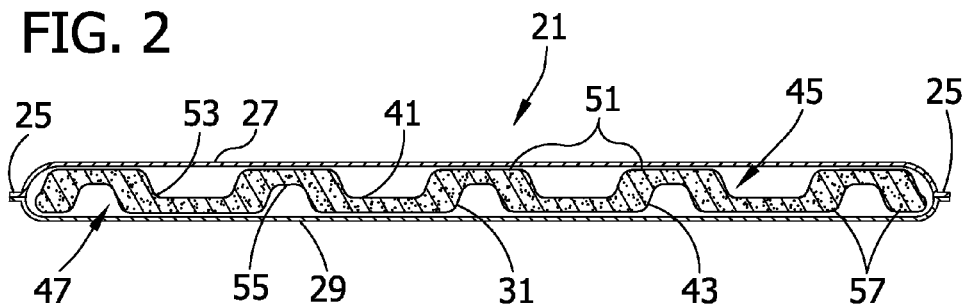
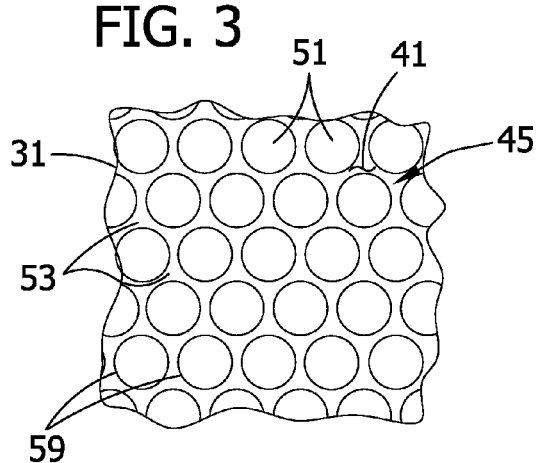
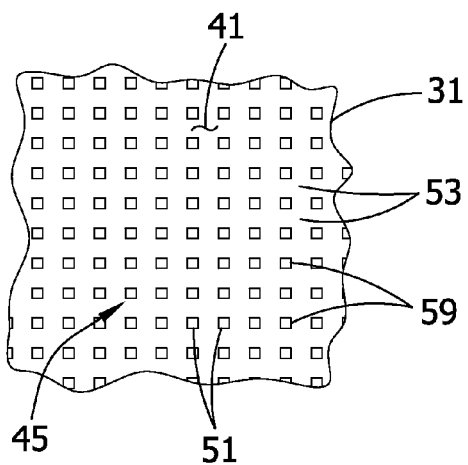

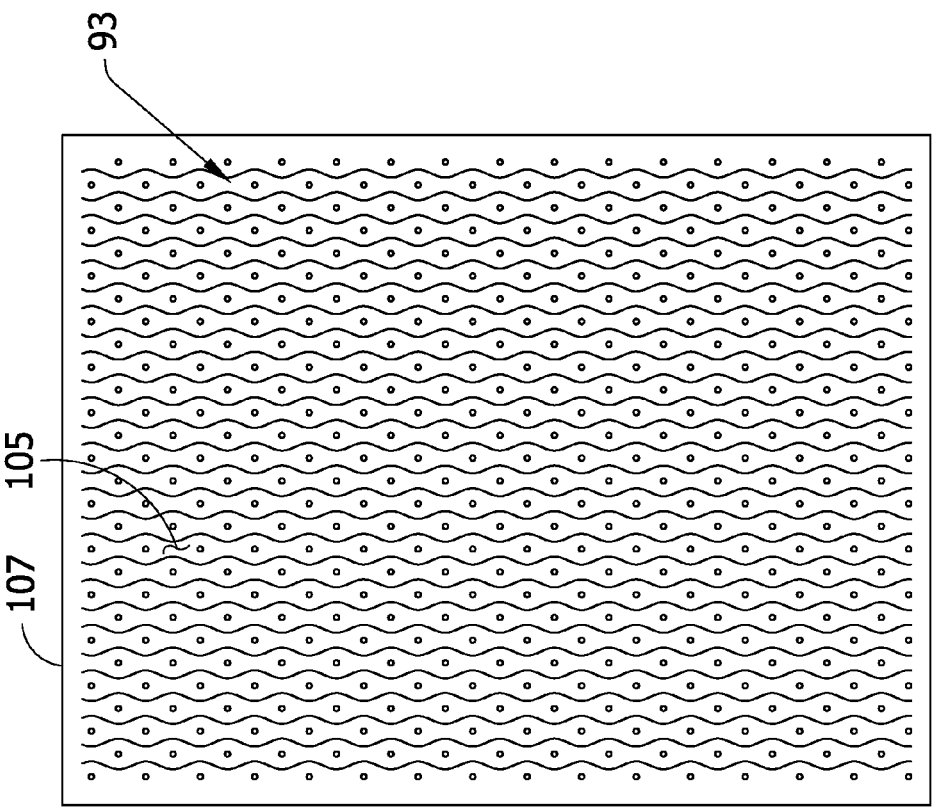
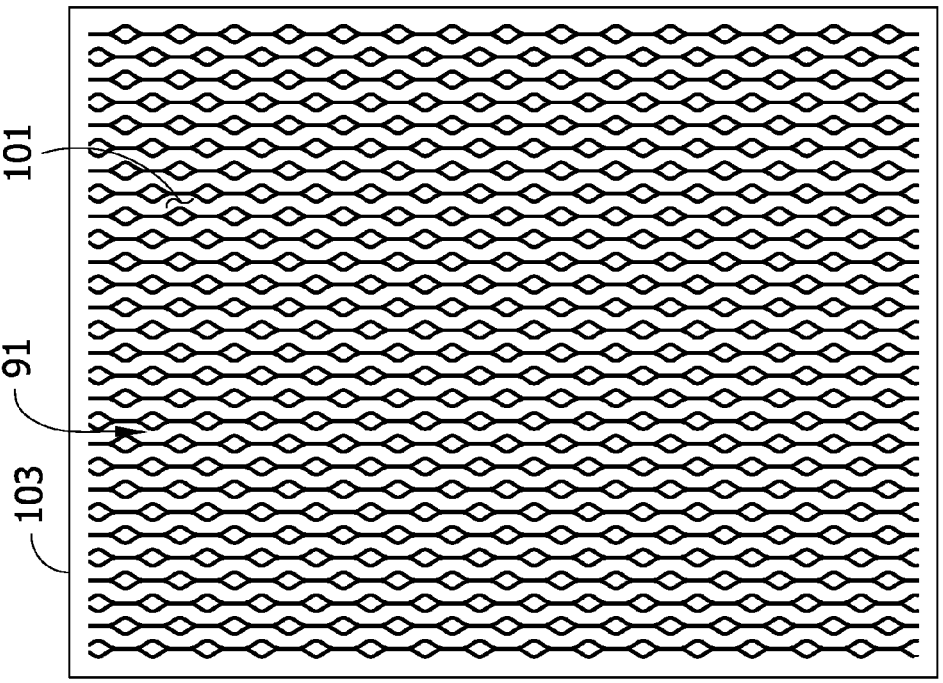

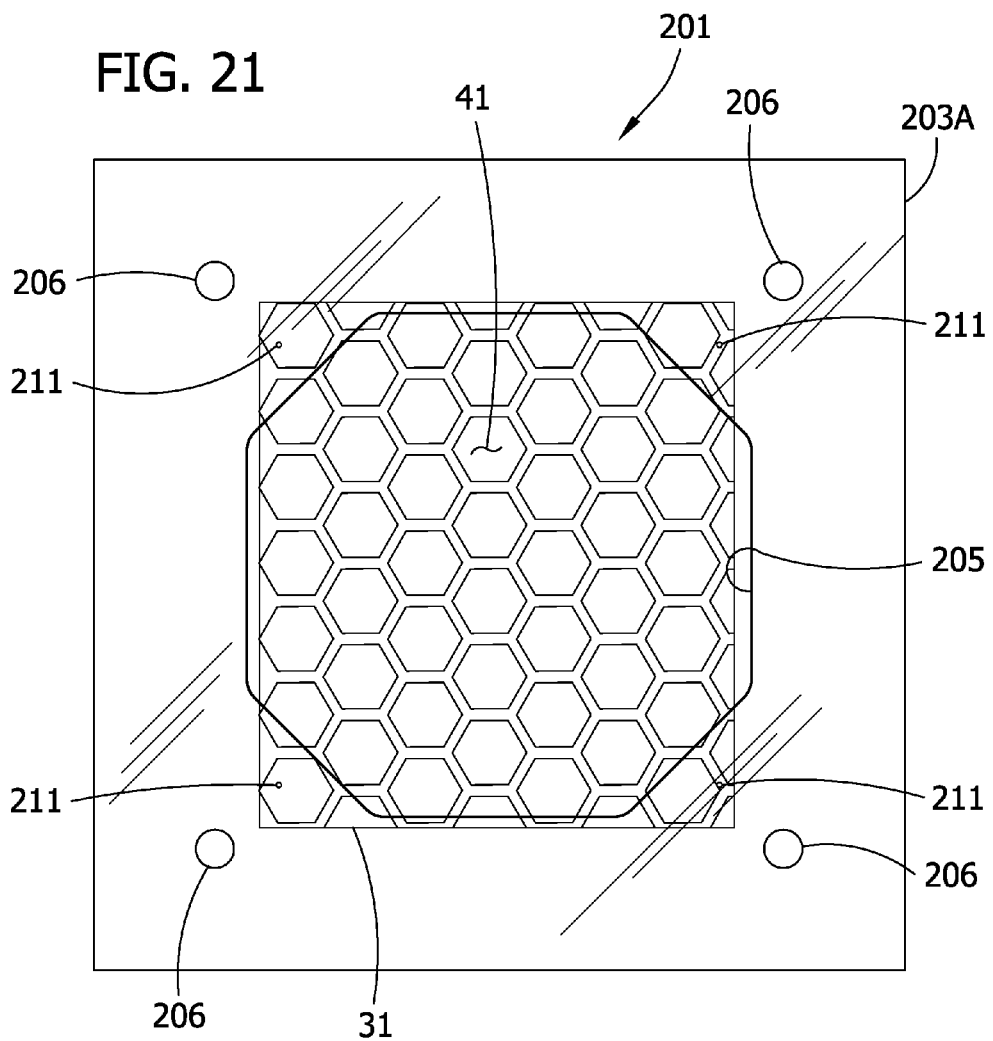
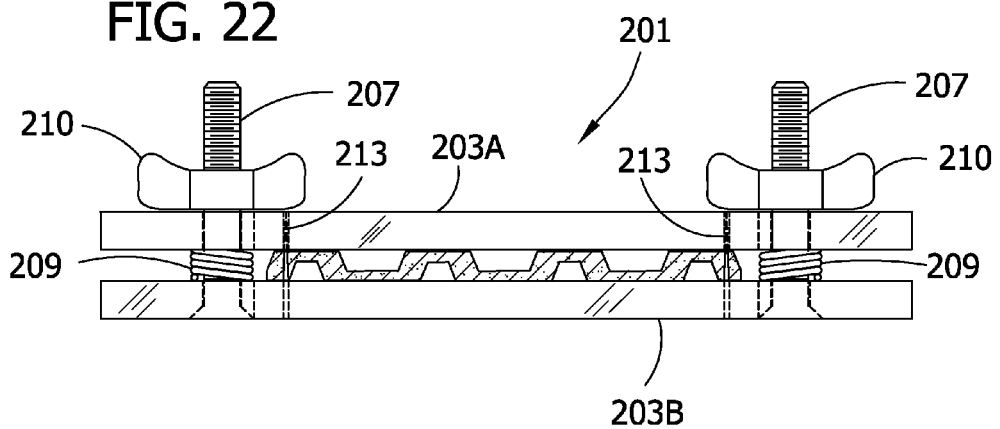

FIG. 24

| Basis Weight (gsm) | Surface Topography | Compression Depth | Projected Area (cm²) | Total Surface Area (cm²/cm²) | Vertical Area (cm²/cm²) | Open Space UnderLoad (cm³/cm²) | Perimeter Under Load (cm/cm²) | Contact Area Under Load (cm²/cm²) | Peak Basis Weight (gsm) | Valley Basis Weight (gsm) |
|---|---|---|---|---|---|---|---|---|---|---|
| 120 | Control | N/A | 6.833 | 1.001 | 0.036 | 0.004 | 0.407 | 0.517 | 114 | 114 |
| 120 | Flat | Half | 6.418 | 1.001 | 0.035 | 0.006 | 0.427 | 0.688 | 123 | 123 |
| 120 | Large Hex | Half | 14.569 | 1.005 | 0.089 | 0.015 | 1.315 | 0.394 | 133 | 124 |
| 120 | Triangles | Half | 6.789 | 1.027 | 0.208 | 0.039 | 1.326 | 0.125 | 114 | 109 |
| 120 | Square | Half | 6.442 | 1.006 | 0.100 | 0.021 | 0.989 | 0.078 | 133 | 135 |
| 120 | Curved Channels | Half | 6.481 | 1.004 | 0.081 | 0.015 | 1.203 | 0.064 | 137 | 144 |
| 120 | Large Hex | Full | 13.982 | 1.055 | 0.253 | 0.036 | 1.085 | 0.444 | 108 | 112 |
| 120 | Triangles | Full | 6.550 | 1.180 | 0.549 | 0.086 | 1.731 | 0.214 | 93 | 101 |
| 120 | Square | Full | 6.813 | 1.108 | 0.429 | 0.076 | 1.435 | 0.123 | 77 | 93 |
| 120 | Curved Channels | Full | 6.863 | 1.034 | 0.230 | 0.025 | 2.369 | 0.270 | 107 | 117 |
| 225 | Control | N/A | 6.621 | 1.000 | 0.024 | 0.000 | 0.364 | 0.887 | 225 | 225 |
| 225 | Flat | Half | 6.720 | 1.000 | 0.022 | 0.000 | 0.959 | 0.899 | 251 | 251 |
| 225 | Large Hex | Half | 14.535 | 1.011 | 0.127 | 0.019 | 1.292 | 0.423 | 227 | 231 |
| 225 | Triangles | Half | 6.544 | 1.068 | 0.342 | 0.075 | 0.692 | 0.042 | 214 | 197 |
| 225 | Square | Half | 6.626 | 1.018 | 0.177 | 0.021 | 2.435 | 0.289 | 216 | 218 |
| 225 | Curved Channels | Half | 6.646 | 1.015 | 0.157 | 0.030 | 0.843 | 0.048 | 235 | 231 |
| 225 | Flat | Full | 6.768 | 1.000 | 0.020 | 0.000 | 0.101 | 0.997 | 224 | 224 |
| 225 | Large Hex | Full | 14.404 | 1.082 | 0.338 | 0.088 | 0.974 | 0.237 | 216 | 219 |
| 225 | Triangles | Full | 6.622 | 1.169 | 0.539 | 0.114 | 0.619 | 0.047 | 162 | 168 |
| 225 | Square | Full | 6.613 | 1.107 | 0.452 | 0.069 | 1.718 | 0.137 | 177 | 177 |
| 225 | Curved Channels | Full | 6.766 | 1.056 | 0.295 | 0.017 | 3.137 | 0.457 | 176 | 177 |

FIG. 25

| Basis Weight (gsm) | Surface Topography | Compression | Intake 1 (sec) | Intake 2 (sec) | Intake 3 (sec) | Rewet (grams) | Standard Dev. Intake 1 | Standard Dev. Intake 2 | Standard Dev. Intake 3 | Standard Dev. Rewet |
|---|---|---|---|---|---|---|---|---|---|---|
| 120 | Control | N/A | 15 | 35 | 101 | 0.54 | 2 | 5 | 32 | 0.06 |
| 120 | Flat | Half | 11 | 30 | 78 | 0.56 | 1 | 4 | 23 | 0.11 |
| 120 | Large Hex | Half | 12 | 25 | 61 | 0.58 | 1 | 4 | 9 | 0.17 |
| 120 | Triangles | Half | 14 | 17 | 31 | 0.60 | 1 | 3 | 6 | 0.07 |
| 120 | Square | Half | 12 | 27 | 70 | 0.58 | 1 | 3 | 15 | 0.09 |
| 120 | Curved Channels | Half | 12 | 24 | 59 | 0.53 | 1 | 4 | 16 | 0.11 |
| 120 | Flat | Full | 23 | 76 | 301 | 0.39 | 4 | 15 | 4 | 0.13 |
| 120 | Large Hex | Full | 12 | 17 | 35 | 0.63 | 2 | 4 | 6 | 0.08 |
| 120 | Triangles | Full | 13 | 10 | 14 | 0.54 | 3 | 2 | 2 | 0.15 |
| 120 | Square | Full | 15 | 12 | 18 | 0.47 | 2 | 3 | 6 | 0.09 |
| 120 | Curved Channels | Full | 13 | 17 | 25 | 0.51 | 2 | 2 | 3 | 0.12 |
| 225 | Control | N/A | 15 | 36 | 105 | 0.37 | 1 | 4 | 34 | 0.09 |
| 225 | Flat | Half | 15 | 32 | 106 | 0.38 | 3 | 5 | 50 | 0.08 |
| 225 | Large Hex | Half | 15 | 28 | 69 | 0.41 | 2 | 4 | 28 | 0.14 |
| 225 | Triangles | Half | 14 | 14 | 18 | 0.40 | 5 | 2 | 3 | 0.11 |
| 225 | Square | Half | 16 | 23 | 50 | 0.38 | 3 | 3 | 8 | 0.09 |
| 225 | Curved Channels | Half | 14 | 22 | 50 | 0.36 | 2 | 4 | 17 | 0.08 |
| 225 | Flat | Full | 21 | 60 | 239 | 0.28 | 4 | 15 | 70 | 0.05 |
| 225 | Large Hex | Full | 22 | 11 | 14 | 0.49 | 2 | 2 | 3 | 0.12 |
| 225 | Triangles | Full | 13 | 10 | 13 | 0.38 | 3 | 1 | 3 | 0.13 |
| 225 | Square | Full | 14 | 10 | 12 | 0.35 | 2 | 1 | 1 | 0.12 |
| 225 | Curved Channels | Full | 15 | 14 | 21 | 0.35 | 3 | 3 | 6 | 0.09 |

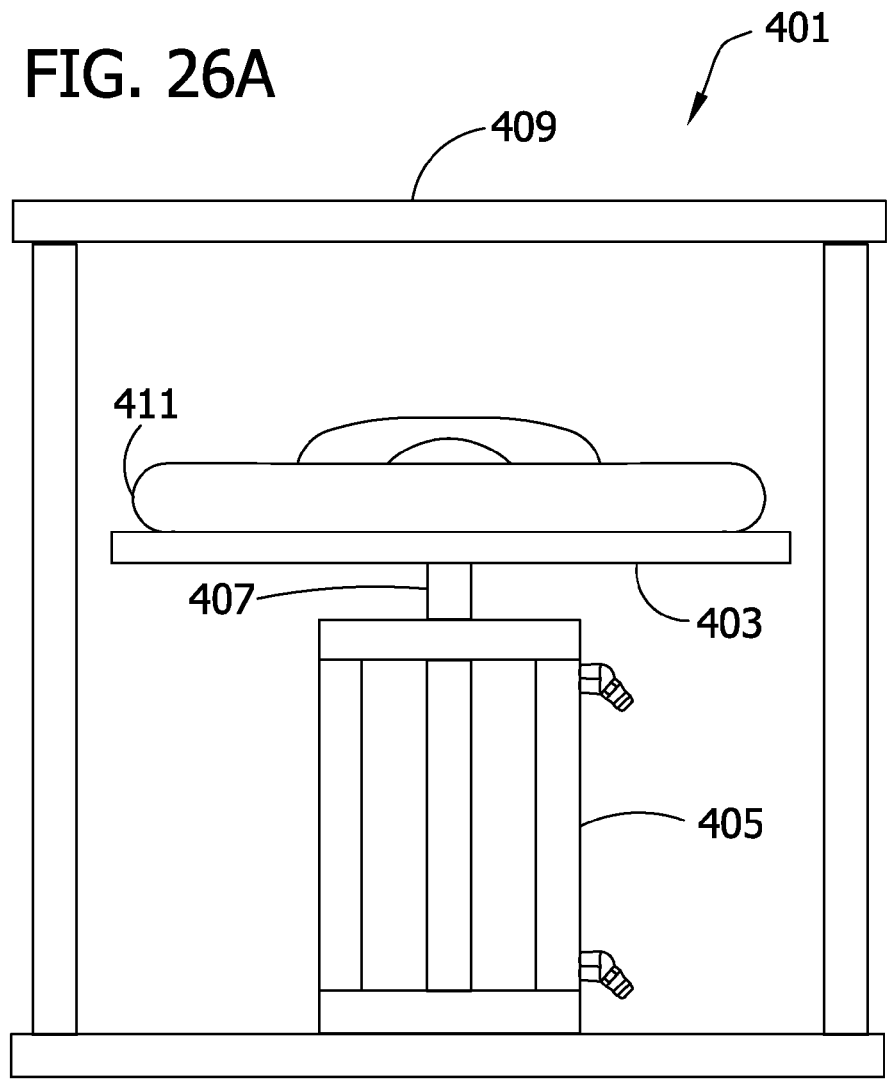

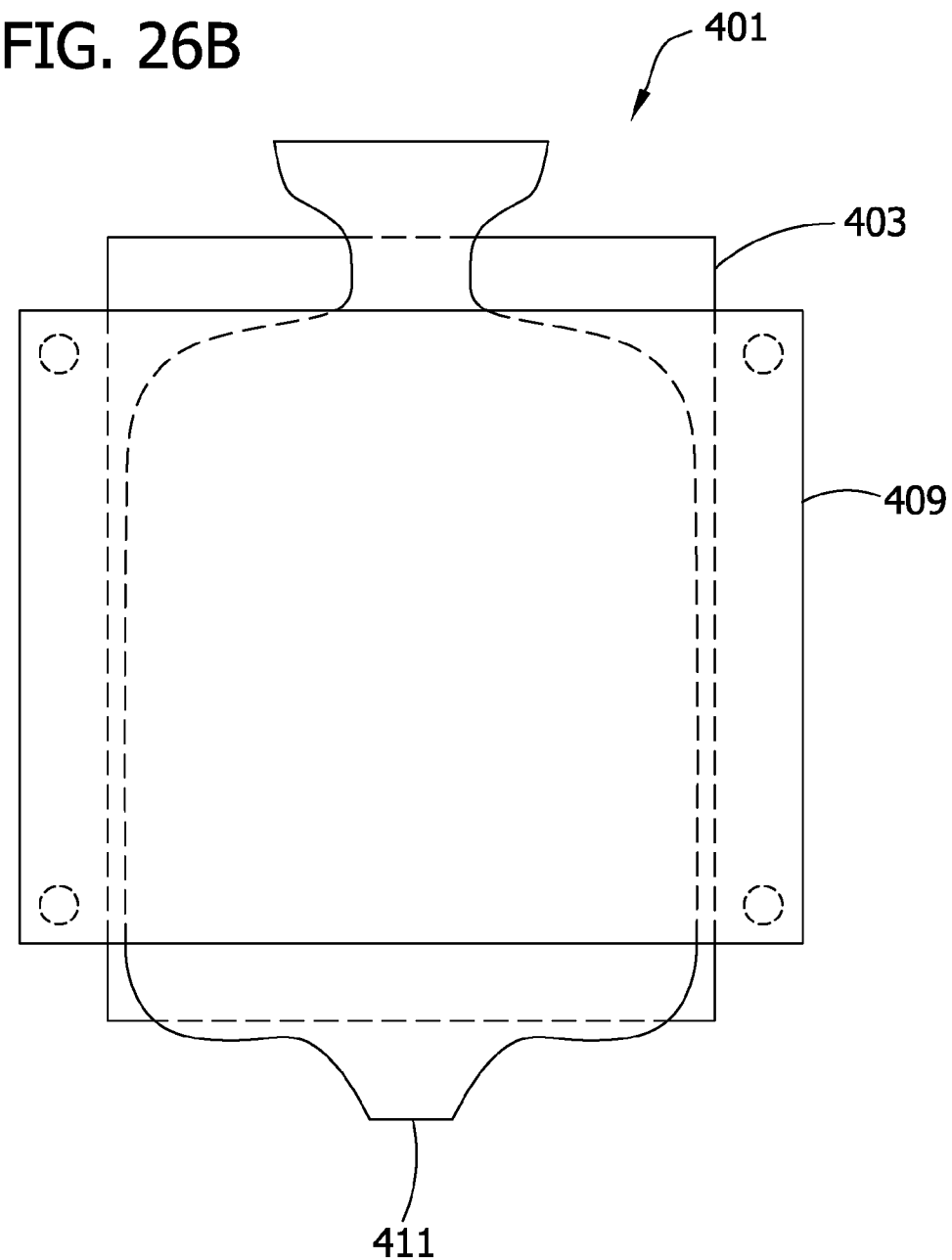

METHOD OF MAKING AN ABSORBENT STRUCTURE HAVING THREE-DIMENSIONAL TOPOGRAPHY

CROSS REFERENCE TO RELATED APPLICATION

This application is a continuation of U.S. patent Ser. No. 10/460,882 filed Jun. 13, 2003, which is hereby incorporated by reference in its entirety.

BACKGROUND OF THE INVENTION

This invention relates generally to absorbent articles used for personal care, such as feminine care articles (e.g., feminine care pads, panty-liners, etc.), diapers, children's training pants, incontinence articles, bandages and the like, and more particularly to such absorbent articles having an absorbent structure that provides for enhanced liquid intake and retention characteristics of such absorbent articles.

Conventional absorbent articles such as feminine care pads typically comprise an absorbent structure disposed between a bodyside liquid-permeable liner and a garment side outer cover, or baffle. The liner and outer cover may extend beyond the absorbent and be bonded together to form a "side edge" or peripheral seal. Some pads further comprise garment attachment panels (e.g., wings or flaps) formed integrally with the liner and/or outer cover and extending laterally outward relative to the intake structure. In use, the pad is placed on the crotch portion of an undergarment such as a panty for taking in and retaining body exudates such as menses, blood and/or urine. The garment attachment panels are folded under and around the crotch portion of the panty and may be secured to each other and/or to the panty crotch portion by suitable adhesive or mechanical fasteners.

The absorbent structure, also sometimes referred to an absorbent body or an absorbent core, may be formed by air-forming, air-laying, co-forming, wet-laying or other known forming technique. For example, the manufacture of such an absorbent structure may begin by fiberizing a fibrous sheet of hydrophilic material in a fiberizer or other shredding or comminuting device to form discrete fibers. In addition, a thermoplastic binder fiber may be mixed with the discrete fibers for subsequent stabilization of the absorbent structure upon heating the binder fibers. In certain absorbent articles, such as training pants and diapers, particles or fibers of super-absorbent materials (also referred to as hydrogel, or hydrocolloid materials), which are water insoluble, water swellable and capable of absorbing at least about ten times their weight in 0.9 weight percent sodium chloride solution in distilled water (saline solution), are also mixed with the fibers. The hydrophilic fibers, binder fibers and (where present) superabsorbent material are then entrained in an air stream and directed to a foraminous forming surface upon which the fibers and superabsorbent material are deposited and accumulated to form the absorbent structure. The absorbent structure may alternatively be a foam, a laminate structure or a combination of layers.

There is a continuing effort by absorbent structure manufacturers to improve the liquid intake performance of absorbent structures as well as the rewet performance thereof. The intake performance refers generally to the ability of the absorbent structure to move fluid through the liner. It is commonly of interest to measure intake with repeated insults thereby measuring the time to absorb as a function of absorbent structure saturation. Rewet generally refers to the ability of the absorbent structure to inhibit previously absorbed liquid against flowing back through the outer surface of the absorbent structure when a compressive load is applied thereto, such as during normal usage including walking, sitting, twisting, etc. The purpose of improving intake performance is to reduce the tendency of the absorbent article to leak during gushes of liquid. A low intake time corresponds with low residence time of liquid on the surface of the product which in turn reduces the likelihood of fluid leakage. Lower rewet corresponds with reduced surface wetness which can improve wearer comfort and helps promote skin health.

However, there is generally considered to be an inverse relationship between the intake performance and the rewet performance of absorbent structures. The reason is generally due to the pore size of the absorbent structure. For example, larger pores allow a faster intake of liquid, but also tend to readily permit flow back of the liquid (rewet) when the absorbent structure is under pressure. Smaller pores more effectively retain liquid, but reduce the rate at which liquid can be taken into the absorbent structure.

There is a need, therefore, for absorbent structures having both improved intake performance and improved rewet performance.

SUMMARY OF THE INVENTION

In one aspect, a method of making an absorbent structure having a three-dimensional topography generally comprises placing at least a portion of the absorbent structure between opposed mold surfaces. At least one of the mold surfaces has a three-dimensional topography. The three-dimensional topography of the mold surface is imparted onto the absorbent structure so that the absorbent structure has a three-dimensional topography corresponding to the three-dimensional topography of the mold surface.

In another aspect, a method of making an absorbent structure having a three-dimensional topography generally comprises passing the absorbent structure through a nip defined by opposed rolls. At least one of the rolls has a mold surface with a three-dimensional topography. The three-dimensional topography of the mold surface is imparted onto the absorbent structure so that the absorbent structure has a three-dimensional topography corresponding to the three-dimensional topography of the mold surface.

In yet another aspect, an absorbent structure has a longitudinal axis, a lateral axis and a z-direction axis normal to the longitudinal and lateral axes. The absorbent structure generally comprises longitudinally opposite ends, laterally opposite side edges, an upper surface, and a lower surface. The upper surface has a three-dimensional topography relative to the longitudinal and lateral axes and defining a plurality of discrete peaks and interconnected valleys of the upper surface relative to the z-direction.

DEFINITIONS

Within the context of this specification, each term or phrase below will include the following meaning or meanings:

"Bi-component," or "Multi-component" fibers as used herein refers to fibers formed from two (e.g., bi-component) or more components, such as a natural fiber and a polymer or two or more polymers extruded from separate extruders, joined together to form a single fiber. The components are arranged in substantially constantly positioned distinct zones across a cross-section of the multi-component fibers and extend continuously along at least a portion of, and more desirably the entire, length of the fiber. The configuration of the multi-component fibers may be, for example, a sheath/ core arrangement in which one polymer is surrounded by another, a side-by-side arrangement, a pie arrangement, an "islands-in-the-sea" arrangement or other suitable arrangement. Bi-component fibers are disclosed in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Bi-component fibers are also taught in U.S. Pat. No. 5,382,400 to Pike et al. and may be used to produce crimp in the fibers by using the differential rates of expansion and contraction of the two (or more) polymers.

"Bonded-Carded" refers to webs that are made from staple length fibers which are sent through a combing or carding unit, which separates or breaks apart and aligns the fibers in the machine direction to form a generally machine direction-oriented fibrous non-woven web. This material may be bonded together by methods that include point bonding, through air bonding, ultrasonic bonding, adhesive bonding or other suitable bonding technique.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface. Coform processes are disclosed in U.S. Pat. No. 5,350,624 to Georger, as well as U.S. Pat. Nos. 5,948,710; 4,100,324; and 3,971,373.

"Hydrophilic" describes a material or surface which can be wetted by aqueous liquids in contact therewith. The degree of wetting can, in turn, be described in terms of the contact angles and the surface tensions of the liquids and materials involved. Equipment and techniques suitable for measuring the wettability of particular materials or surfaces can be provided by a Cahn SFA-222 Surface Force Analyzer System, or a substantially equivalent system. When measured with this system, materials or surfaces having contact angles less than 90 degrees are designated "wettable" or hydrophilic, and those having contact angles greater than 90 degrees are designated "nonwettable" or hydrophobic.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed melt-blown fibers. Such a process is disclosed, for example, in U.S. Pat. No. 3,849,241 to Butin et al, which is incorporated herein by reference. Meltblown fibers are typically microfibers which may be continuous or discontinuous, are generally about 0.6 denier or smaller, and are generally self bonding when deposited onto a collecting surface.

"Non-woven" or "non-woven web" refers to materials or webs that are formed without the aid of a textile weaving or knitting process. Non-woven structures have been formed from many processes such as, for example, meltblowing processes, spunbonding processes, and bonded-carded processes.

"Spunbond" refers to small diameter fibers which are formed by extruding molten thermoplastic material as filaments from a plurality of fine capillaries of a spinneret having a circular or other configuration, with the diameter of the extruded filaments then being rapidly reduced by an air-drawing process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers of about 0.3 or larger, more particularly, between about 0.6 and about 10.

"Superabsorbent" and "Superabsorbent Material" refer to a water-swellable, water-insoluble organic or inorganic material capable, under the most favorable conditions, of absorbing at least about 10 times its weight and, more suitably, at least about 20 times its weight in an aqueous solution containing 0.9 weight percent sodium chloride solution in water. Such materials are described in U.S. Pat. No. 5,147,343 to Kellenberger.

"Thermoplastic" describes a material that softens when exposed to heat and which substantially returns to a non-softened condition when cooled to room temperature.

BRIEF DESCRIPTION OF THE DRAWINGS

FIG. 1 is a perspective of one embodiment of an absorbent article of the present invention in the form of a feminine care pad;

FIG. 2 is a cross-section taken in the plane of line 2-2 of FIG. 1;

FIG. 3 is a fragmented top plan of an absorbent structure of the absorbent article of FIG. 1 illustrating a three-dimensional topography of an upper surface of the absorbent structure;

FIG. 4 is view similar to FIG. 3 illustrating a second embodiment of a three-dimensional topography of the upper surface of the absorbent structure;

FIGS. 18A and 18B are a fourth embodiment of respective upper and lower mold plates having mold surfaces for imparting a three-dimensional topography to upper and lower surfaces of an absorbent structure of the present invention;

FIG. 21 is a top plan of a sample holder used for holding an absorbent structure sample in a scanning device;

FIG. 22 is a side elevation thereof;

FIG. 24 is a table of data obtained from conducting a Topography Analysis Method on various absorbent structures formed in accordance with the present invention;

FIG. 25 is a table of data obtained from conducting an Intake and Rewet Test on various absorbent structures formed in accordance with the present invention;

FIG. 26A is a schematic side elevation of a test stand for conducting an Intake and Rewet Test; and FIG. 26B is a top plan view of the test stand of FIG. 26A.

Corresponding reference characters indicate corresponding parts throughout the drawings.

DETAILED DESCRIPTION

Figure 5:
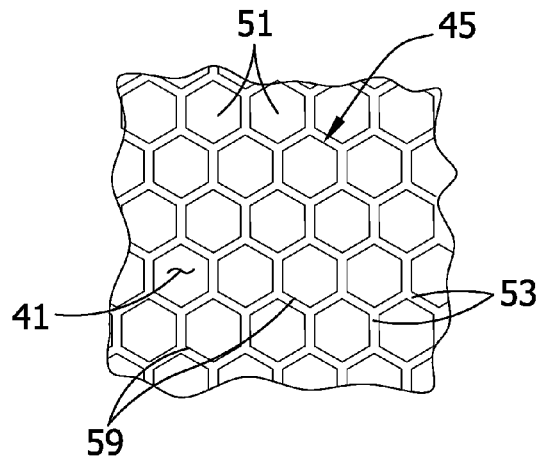
FIG. 5 is view similar to FIG. 3 illustrating a third embodiment of a three-dimensional topography of the upper surface of the absorbent structure.
Figure 6:
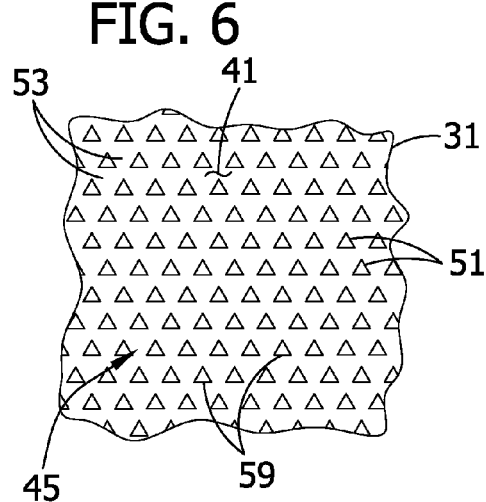
FIG. 6 is view similar to FIG. 3 illustrating a fourth embodiment of a three-dimensional topography of the upper surface of the absorbent structure.

Referring now to the drawings and in particular to FIG. 1, one example of an absorbent article constructed in accordance with the present invention is illustrated in the form of a feminine care pad, which is indicated generally by the reference numeral 21. As used herein, an absorbent article refers to an article which may be placed against or in proximity to the body of the wearer (e.g., contiguous to the body) to absorb and/or retain various exudates discharged from the body. The absorbent article may or may not be disposable, which refers to articles that are intended to be discarded after a limited period of use instead of being laundered or otherwise restored for reuse. It is understood that the principles of the present invention may be incorporated into various absorbent articles other than feminine care pads, including without limitation children's training pants, diapers and other infant and child care products, adult incontinence garments and other adult care products, medical garments, other feminine care products such as panty-liners and the like, as well as surgical bandages and the like.

The pad 21 generally has a lengthwise, or longitudinal axis X, a transverse, or lateral axis Y, a thickness or z-direction axis Z, longitudinally opposite ends 23, and laterally opposite side edges 25. As representatively shown, the longitudinal dimension (e.g., length) of the pad 21 is relatively larger than the lateral dimension (e.g., width) thereof. The pad 21 comprises a bodyside liner 27 which faces the wearer's body in use, e.g., in contiguous relationship therewith, an outer cover 29 which faces away from the wearer's body, and an absorbent structure 31 (FIG. 2) disposed between the liner and the outer cover.

The liner 27 is suitably pliable, soft feeling, and nonirritating to the wearer's skin, and is employed to help isolate the wearer's skin from the absorbent structure 31. In one embodiment, the liner 27 may be less hydrophilic than the absorbent structure 31 to present a relatively dry surface to the wearer, and is sufficiently porous to be liquid permeable to thereby permit liquid to readily penetrate through its thickness. A suitable bodyside liner 27 may be manufactured from a wide selection of web materials. Various woven and non-woven fabrics including synthetic and/or natural fibers can be used for the liner 27. Examples of suitable non-woven fabrics include spunbond fabrics, meltblown fabrics, co-form fabrics, carded webs, bonded-carded-webs, bicomponent spunbond fabrics or the like and combinations thereof.

Alternatively, the liner 27 may be a polymer film, a film-fabric laminate or other suitable material such as rayon, bonded carded webs of polyester, polypropylene, polyethylene, nylon, or other heat-bondable fibers, polyolefins such as copolymers of polypropylene and polyethylene, linear low-density polyethylene, aliphatic esters such as polylactic acid, finely perforated film webs, net materials and combinations thereof. The liner 27 may also be a composite of a polymer and a non-woven fabric material. Such composite materials are typically in the form of integral sheets generally formed by the extrusion of a polymer onto a web of spunbond material. As an example, one particularly suitable liner 27 material is a bonded-carded-web comprised of polypropylene and polyethylene.

The liner 27 can also have at least a portion thereof treated with a surfactant to render the liner more hydrophilic. The surfactant can permit liquid, e.g., menses, blood, urine, etc. to more readily penetrate the liner 27 for flow to the absorbent structure 31. The surfactant may also reduce the likelihood that the body liquids will run off the liner 27 rather than permeate therethrough to the absorbent structure 31.

The outer cover 29 suitably comprises a material that is liquid impermeable and vapor permeable, and may be elastic, stretchable or non-stretchable. For example, the outer cover 29 may be a polymeric film, a woven fabric, a non-woven fabric and/or combinations or composites thereof. In one embodiment, the outer cover 29 can be a laminate structure having an inner layer of polymer film laminated to an outer layer of woven or non-woven fabric. The polymer film can be composed of polyethylene, polypropylene, polyester or other suitable polymers and combinations thereof. Additionally, the polymer film may be micro-embossed. One example of a suitable outer cover 29 material is a breathable, microporous film, such as a material commercially available from Hanjin Printing, Hanjin P&C Company Limited of Sahvon-li.Jungan-mvu.Kongiu-City, Chung cheong nam-do, Republic of South Korea, under the tradename HANJIN Breathable Baffle. The material is a breathable film that is white in color, dimple embossed, and contains: 47.78% calcium carbonate, 2.22% TiO2 and 50% polyethylene. Another example outer cover 29 material is a polyethylene film used on commercially sold KOTEX brand panti-liners and commercially available from Pliant Corporation of Schaumburg, Ill., USA. Bicomponent films or other multi-component films can also be used, as well as woven and/or nonwoven fabrics which have been treated to render them substantially liquid-impermeable. Alternatively, the outer cover 29 material may be a closed cell polyolefin foam.

The liner 27 and/or outer cover 29 may be secured to the absorbent structure 31 by bonding all or a portion of the adjacent surfaces to one another. A variety of bonding techniques known to one of skill in the art may be utilized to achieve any such secured relationship. Examples of such bonding techniques include, but are not limited to, the application of adhesives in a variety of patterns between the two adjoining surfaces, entangling at least portions of the adjacent surfaces, or fusing together at least portions of the adjacent surfaces.

The liner 27 typically extends over the upper, bodyside facing surface of the absorbent structure 31, but can alternatively partially or entirely surround or enclose the absorbent structure. Alternatively, as shown in FIG. 2, the liner 27 and the outer cover 29 can have peripheral margins which extend outwardly beyond the terminal, peripheral edges of the absorbent structure 30, and the extending margins can be joined together to partially or entirely surround or otherwise enclose the absorbent structure.

In one embodiment, the absorbent structure 31 is suitably a non-woven web comprising absorbent fibers and binder material. Examples of suitable absorbent fibers include hydrophilic fibers including without limitation naturally occurring organic fibers composed of intrinsically wettable material, such as cellulosic fibers. Suitable sources of cellulosic fibers include: wood fibers, such as bleached kraft softwood or hardwood, high-yield wood fibers, and ChemiThermoMechanical Pulp fibers; bagasse fibers; milkweed fluff fibers; wheat straw; kenaf; hemp; pineapple leaf fibers; or peat moss. Other hydrophilic fibers, such as regenerated cellulose and curled chemically stiffened cellulose fibers may also be densified to form absorbent structures that can expand to a higher loft when wetted. Pulp fibers may also be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. One example of a suitable hydrophilic fiber is available from Weyerhauser of Federal Way, Wash., U.S.A. as model designation NF-401 and is a partially debonded Kraft pulp.

Other examples of suitable hydrophilic fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing a nonwettable, hydrophobic fiber with a hydrophilic polymer during or after the formation of the fiber. For the purposes of the present invention, it is contemplated that selected blends of the various types of fibers mentioned above may also be employed.

In one embodiment, the binder material suitably comprises thermoplastic binder fibers which are activatable, such as upon the application of heat, to form inter-fiber bonds within the absorbent structure 31 for stabilizing the absorbent structure. The inter-fiber bonds may be formed between the binder fibers and the absorbent fibers and/or between the binder fibers themselves. As an example, the binder fibers may suitably comprise bicomponent, or multicomponent binder. In other embodiments, the binder fibers can be monofilament or homofilament fibers, biconstituent fibers and the like, as well as combinations thereof. One example of a suitable bicomponent binder fiber is commercially available from KoSa of Houston, Tex., U.S.A. as model designation T255. Other suitable binder fiber materials are disclosed in International Publication No. WO 01/26595 (Chen et al.) entitled Absorbent Articles With Molded Cellulosic Webs, published Apr. 19, 2001.

The concentration of absorbent fibers in the absorbent structure 31 is suitably in the range of about 5% to about 98% by weight of the absorbent structure, and more suitably about 90% by weight thereof. The binder fiber concentration is suitably in the range of about 2% to about 95% by weight of the absorbent structure 31, and more suitably about 10% by weight thereof.

It is contemplated that the binder material may alternatively, or may additionally, be a powder or other particulate form. Binder powders for use in absorbent structures are available under the trade name VINNEX, which is available from Wacker Polymer Systems L.P., having offices in Adrian, Mich., U.S.A.

As an alternative to the binder fiber and/or particulates, or in addition thereto, a class of materials described herein as "latex binders" may be used as the binder material. Examples of such latex binders include, but are not limited to, emulsion polymers such as thermoplastic vinyl acetate, C1-C8 alkyl ester of acrylic, methacrylic acid based adhesive, and combinations thereof. In particular, the emulsion polymerized thermoplastic adhesive can have a Tg from −25° C. to 20° C., a solids content of from 45% to 60% by weight, typically from 52% to 57%, and a Brookfield viscosity (#4 spindle, 60 rpm at 20° C.) of from 5 to 1000 centipoises (cps). Preferred adhesives are vinyl acetate/ethylene based adhesives incorporating less than about 10% and preferably less than 5% by weight, of a polymerized third monomer.

Representative examples of third monomers which may be incorporated into the polymer include adhesion promoting monomers such as unsaturated carboxylic acid including acrylic and methacrylic acid, crotonic acid, and epoxide containing monomers such as glycidyl acrylate, glycidylmethacrylate and the like. The Airflex 401, 405 and 410 are some examples. These binders can be obtained from Air Products and Chemicals Inc. located in Allentown, Pa., U.S.A. In addition, cross linkable binders (thermoset) may be used to impart further wet strength thereto. The thermoset vinyl acetate/ethylene binders, such as vinyl acetate/ethylene having from 1-3% N-methylolacrylamide such as Airflex 124, 108 or 192, available from Air Products and Chemicals Inc. located in Allentown, Pa., or Elite 22 and Elite 33, available from National Starch & Chemicals, located in Bridgeport, N.J., are examples of suitable adhesive binders.

In use, emulsion polymerized thermoplastic polymeric adhesive is applied to a web of absorbent fibers in an amount ranging from about 1 to about 20 grams dry adhesive per square meter of the web. In particular aspects, about 5 to about 15 grams of dry adhesive per square meter of web is applied where the dry adhesive is applied by a spray method.

It is contemplated that in certain embodiments the absorbent structure 31 may additionally comprise a superabsorbent material. The superabsorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. The term "crosslinked" as used in reference to the superabsorbent material refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces. The superabsorbent material may be present in the absorbent structure, 31, in the range of about 0 to about 78%, more suitably from about 0 to about 65%, and even more suitably from about 0 to about 50%. Suitable superabsorbent materials are available from various commercial vendors such as The Dow Chemical Company, BASF Corporation, Allied Colloid Inc., and Stockhausen, Inc.

Other superabsorbent material morphologies are also applicable for use in these absorbent structures. Superabsorbent fibers like those manufactured by Camelot Superabsorbents Limited of High River, Alberta Canada can be added homogeneously or heterogeneously in the non-woven web. In addition, superabsorbents can be produced directly on the absorbent structure by applying an appropriate monomer solution on the absorbent structure and polymerizing it using some suitable means such as heat (used with thermal initiators) or UV light (for use with UV initiators), or electron beam.

In other embodiments, the absorbent structure may suitably be formed without binder material and/or superabsorbent material and remain within the scope of this invention.

With particular reference to FIG. 2, the absorbent structure 31 is formed to have a three dimensional topography on both an upper (e.g., liner facing) surface 41 and a lower (e.g., outer cover facing) surface 43 of the absorbent structure. As used herein, the three-dimensional topography is intended to mean that the upper and lower surfaces 41, 43 of the absorbent structure 31 each have pronounced, z-direction (e.g., the thickness direction) surface features, generally indicated respectively at 45, 47, projecting inward and/or outward relative in the z-direction relative to the plane defined by the longitudinal and lateral axes of the absorbent structure. For example, the three-dimensional topography of the upper surface 41 of the absorbent structure 31 shown in FIG. 2 has a plurality of peaks 51 and valleys 53 wherein the height (e.g., z-direction difference) between the peaks and their respective adjacent valleys is greater than that of nominal surface variations resulting from manufacturing tolerances, such as at least about 0.9 mm when the absorbent structure is under a load of about 0.05 psi (about 0.345 kPa) as described later herein. The three-dimensional topography of the lower surface 43 of the absorbent structure 31 also has a plurality of peaks 55 and valleys 57 having a similar minimum height (e.g., z-direction difference therebetween).

In the illustrated embodiment, the locations of the peaks 51 of the upper surface 41 correspond generally to the locations of respective peaks 55 of the lower surface 43 and the locations of the valleys 53 of the upper surface correspond generally to the locations of respective valleys 57 of the lower surface. However, it is understood that the shapes, height, etc. of the upper surface peaks 51 and valleys 53 need not be identical or otherwise similar to the corresponding lower surface peaks 55 and valleys 57. It is also understood that the locations of the upper surface peaks 51 and valleys 53 need not correspond to the locations of the lower surface peaks 55 and valleys 57 to remain within the scope of this invention, as long as both the upper and lower surfaces 41, 43 of the absorbent structure each have a three dimensional topography. Also, the three-dimensional topography of the upper and lower surfaces 41, 43 may extend fully or it may extend only partially across the width and/or along the length of the absorbent structure 31.

Figure 7:
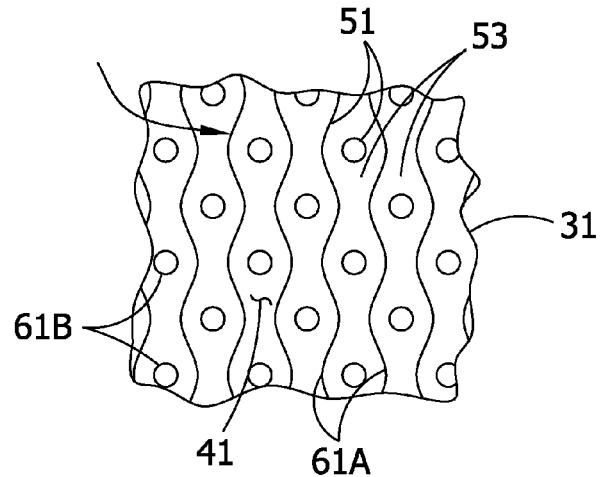
FIG. 7 is view similar to FIG. 3 illustrating a fifth embodiment of a three-dimensional topography of the upper surface of the absorbent structure.

The peaks 51, 55 of the upper and lower surfaces 41, 43 of the absorbent structure 31 may be in the form of discrete peaks surrounded by interconnected valleys (e.g., the valleys are generally continuous). As an example, FIGS. 3, 4, 5, 6 illustrate various absorbent structures 31 in which the upper surface 41 has a plurality of surface features 45 in the form of discrete bumps 59 defining discrete peaks 51 and generally continuous or otherwise interconnected valleys 53 of the upper surface. In FIG. 3, the bumps are generally circular in horizontal cross-section; in FIG. 4 the bumps are generally square in horizontal cross-section; in FIG. 5 the bumps are generally hexagonal in horizontal cross-section; and in FIG. 6 the bumps are generally triangular in horizontal cross-section. In another embodiment shown in FIG. 7, the surface features 45 of the upper surface 41 include bumps in the form of ridges 61a extending in a serpentine manner generally continuously along the length of the absorbent structure. Additional discrete bumps 61b are disposed intermediate the ridges 61a. It is also contemplated that other three-dimensional surface patterns are within the scope of this invention, as long as the upper and lower surfaces 41, 43 of the absorbent structure 31 each have a plurality of peaks 51, 55 and valleys 53, 57. For example, the peaks of the upper surface (and/or the lower surface) may be interconnected (e.g., the peaks may be generally continuous) and surrounded by discrete valleys.

Also, the pattern defined by the three-dimensional topographies of the upper surfaces 41 shown in each of 3-7 are generally uniform, repeating patterns both across the width and along the length of the absorbent structure 31. However, it is contemplated that the pattern defined by the three-dimensional topography may be non-repeating in one or both of the longitudinal and lateral directions of the absorbent structure 31. For example, the size, shape, number, etc. of the surface features 45, 47 may vary along the width and/or length of the absorbent structure 31. It is also contemplated that the pattern of surface features 45, 47 on the upper surface 41 and/or lower surface 43 may be generally random without departing from the scope of this invention.

The height of the surface features 45 on the upper surface 41 of the absorbent structure 31, as measured from one peak 51 to an adjacent valley 53 with the absorbent structure unloaded, is suitably at least about 1 mm, and more suitably in the range of about 1.5 mm to about 5 mm. The surface features 47 on the lower surface 43 suitably have a height within this range. As an example, the height of the square bumps 59 shown on the upper surface 41 of the absorbent structure 31 of FIG. 4 is about 1.4 mm as is the height of the serpentine ridges 61a shown on the upper surface of the absorbent structure of FIG. 7.

The surface feature density of the upper surface 41 of the absorbent structure 31, e.g., the number of bumps or other surface features 45 per square cm of upper surface, is suitably measured by first evaluating the pattern of surface features to determine a "minimum repeat area" that can be used to recreate the entire upper surface. For the case of unique or otherwise non-repeating patterns that comprise the entire upper surface, the entire upper surface comprises the minimum repeat area. The number of surface features present within the minimum repeat area is divided by the projected area of the minimum repeat area. The term projected area refers to an area corresponding to a flat area (e.g., in the horizontal plane) that would be covered if the absorbent structure 31 were laid on a flat surface.

The surface feature density is suitably at least about 0.1 features per square cm of projected area, and is more suitably in the range of about 0.2 to about 10 surface features per square cm of projected area. It is understood, however, that the surface feature height and or density may be other than as set forth above without departing from the scope of this invention, as long as the surface feature density is at least about 0.1 surface features per square centimeter of projected area.

In one embodiment, the absorbent structure 31 has a generally uniform basis weight whereby the basis weight of the absorbent structure at the peaks 51 of the upper surface 41 is substantially equal to the basis weight of the absorbent structure at the valleys 53 of the upper surface. The term "substantially equal" in reference to the basis weight of the absorbent structure 31 at the peaks 51 and valleys 53 of the upper surface 41 is intended to mean that the basis weights are within approximately 10 percent of each other. The average basis weight of the absorbent structure 31 is suitably in the range of about 60 grams per square meter (gsm) to about 1500 gsm, and more suitably in the range of about 120 gsm to about 225 gsm. However, it is contemplated that the basis weight of the absorbent structure 31 at the peaks 51 of the upper surface 41 may instead be greater than or less than (e.g., by more than about 10 percent) the basis weight of the absorbent structure at the valleys 53 of the upper surface.

The density of the absorbent structure 31 at the peaks 51 and valleys 53 of the upper surface 41 generally depends on whether the basis weight is substantially uniform and also depends on the relative size and shape of the peaks 51 and valleys 53 of the upper surface compared to the size and shape of the peaks 55 and valleys 57 of the lower surface 43. In general, the density of the absorbent structure is suitably in the range of about 0.06 grams per cubic centimeter (g/cc) to about 0.40 g/cc, and more suitably in the range of about 0.10 g/cc to about 0.20 g/cc. The density of the absorbent structure 31 at the peaks 51 of the upper surface 41 may be greater than, less than or otherwise about equal to the density of the absorbent structure at the valleys 53 of the upper surface without departing from the scope of this invention.

In another embodiment, the absorbent structure topography is combined with a liner material that has surface topography. The topography of the liner may or may not be similar in design, scale, or orientation to the topography of the absorbent structure. These liner/absorbent structure combinations require alternate methods for calculating open space under load, contact area under load, and contact perimeter under load due to the fact that the cover is not planer. Such modifications to the methods can be made by those skilled in the art. These structures have reduced contact with the user's skin and can therefore further reduce rewet and help maintain skin health.

In accordance with the present invention, the three-dimensional topography of the upper surface 41 of the absorbent structure 31 also defines certain characteristics as determined by the Topography Analysis Method set forth below.

Topography Analysis Method

The Topography Analysis Method described herein is a mathematical characterization of the three-dimensional topography of the upper and/or lower surfaces 41, 43 of the absorbent structure 31. The method generally utilizes a three dimensional laser scanning of the upper and lower surfaces 41, 43 of the absorbent structure 31 to generate a point cloud comprising a plurality of spatial points which accurately depict the topography of the upper and lower surfaces. Scanning is completed on both the upper and lower surfaces so that the relative positions of both surfaces are accurately represented in the point cloud.

Absorbent structures on which the Topography Analysis Method may be performed are suitably formed to resist substantial collapse under load (e.g., when a load is applied to the upper and/or lower surfaces 41, 43 of the absorbent structure). Collapse refers to a situation in which a portion of a surface feature of the absorbent structure obscures any other portion of the surface feature when under a pressure of 0.05 psi (about 0.345 kPa) and viewed from directly above. The absorbent structures described later herein for which the Topography Analysis Method was performed all satisfy this criterion. However, it is understood that simple modifications to the Topography Analysis Method can be made to account for absorbent structures that collapse under such a load.

The spatial points are then used to define a plurality of triangles which map the topography of the upper and lower surfaces 41, 43, wherein each triangle shares two vertices with an adjacent triangle. As an example of the resolution of the data, the triangles suitably have an average side length of about 0.035 cm.

The data describing the triangles is stored in at least two different "STL" data files, with one STL data file containing only the data describing the triangles for the upper surface 41 of the scanned absorbent structure 31 and another STL data filed containing the data describing the triangles for both the upper and lower surfaces 41, 43 of the absorbent structure. It is contemplated that a third STL data filed containing the data describing the triangles for only the lower surface 43 of the absorbent structure 31 may also be generated. The triangle vertices are represented in the STL data file in a standard Cartesian coordinate system.

Each STL data file has the following format:

| Size | Format | Description |
| --- | --- | --- |
| 80 bytes | ASCII | File Description Header |
| 4 bytes | Unsigned long integer | Number of triangles in the file |
| 4 bytes | Float | I component of normal vector |
| 4 bytes | Float | J component of normal vector |
| 4 bytes | Float | K component of normal vector |
| 4 bytes | Float | x component of Point 1 vertex |
| 4 bytes | Float | y component of Point 1 vertex |
| 4 bytes | Float | z component of Point 1 vertex |
| 4 bytes | Float | x component of Point 2 vertex |
| 4 bytes | Float | y component of Point 2 vertex |
| 4 bytes | Float | z component of Point 2 vertex |
| 4 bytes | Float | x component of Point 3 vertex |
| 4 bytes | Float | y component of Point 3 vertex |
| 4 bytes | Float | z component of Point 3 vertex |
| 2 bytes | Unsigned integer | Attribute byte count |

The outer surface of the triangle (e.g. the surface of the triangle that faces outward of the absorbent structure 31) is defined as that surface of the triangle where the vertices are arranged counterclockwise from point 1 to point 2 to point 3. A mathematically synonymous way to determine the outer surface of the triangle is to define a vector normal to the triangle as the normalized cross product of the vectors point 2−point 1 and point 3−point 1. Adhering to this criterion is mandatory for using the analytical code attached hereto as Appendices A and B and described later herein to analyze the STL data files. The order of the points in the STL data files is used repeatedly to determine the orientation of the triangles. It is also important that the scanning be performed with the absorbent structure oriented generally along the X, Y plane whereby the absorbent structure thickness is generally aligned with the Z axis. Additionally the user facing surface (upper surface) must be set such that it faces in the positive Z direction. One suitable scanning of absorbent structures and generation of corresponding STL data files is commercially performed by Laser Design Incorporated of Minneapolis, Minn., U.S.A.

One analytical code, which is attached hereto as Appendix A, is used to read the STL data file for the upper surface 41 of the scanned absorbent structure 31 and to mathematically analyze various characteristics of the upper surface. The Appendix A code is suitable for use with a software package commercially available from Wolfram Research, Inc. of Champaign, Ill., U.S.A under the tradename Mathematica. The Appendix A code (and Appendix B code described later herein) was generated and processed using Mathematica version 4.2. In particular, with reference to the Appendix A code and to FIG. 8, the center of each triangle in the upper surface 41 STL data file is determined and a simple regression fit is used to fit the center points of the triangles to the equation $Z=B0+B1*X+B2*Y$. This equation defines a plane, referred to in the Appendix A code and indicated in FIG. 8 as the "Best Fit Plane," for the upper surface 41 of the absorbent structure 31. Next, a base point is defined on the Best Fit Plane and a vector (referred to in the Appendix A code as "PlaneNorm") normal to the Best Fit Plane (e.g., in the z-direction) is determined. Of the two normal vectors to the best fit plane, the one most closely aligned to the positive Z axis is chosen. The distance from the center of each triangle to the Best Fit Plane is then calculated, with positive distances being in the direction of the normal vector (e.g., PlaneNorm) and negative distances being in the opposite direction of the normal vector.

Figure 8:
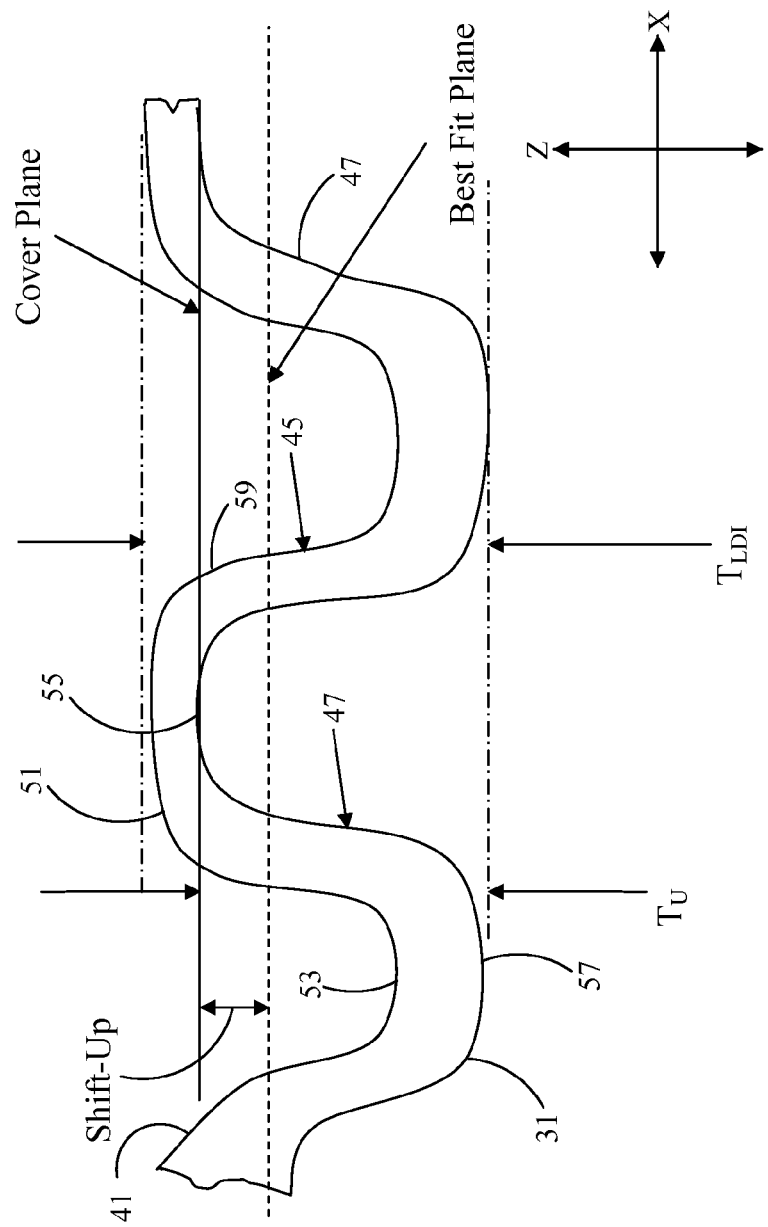
FIG. 8 is a schematic cross-section of the absorbent structure of FIG. 2.
Figure 9:
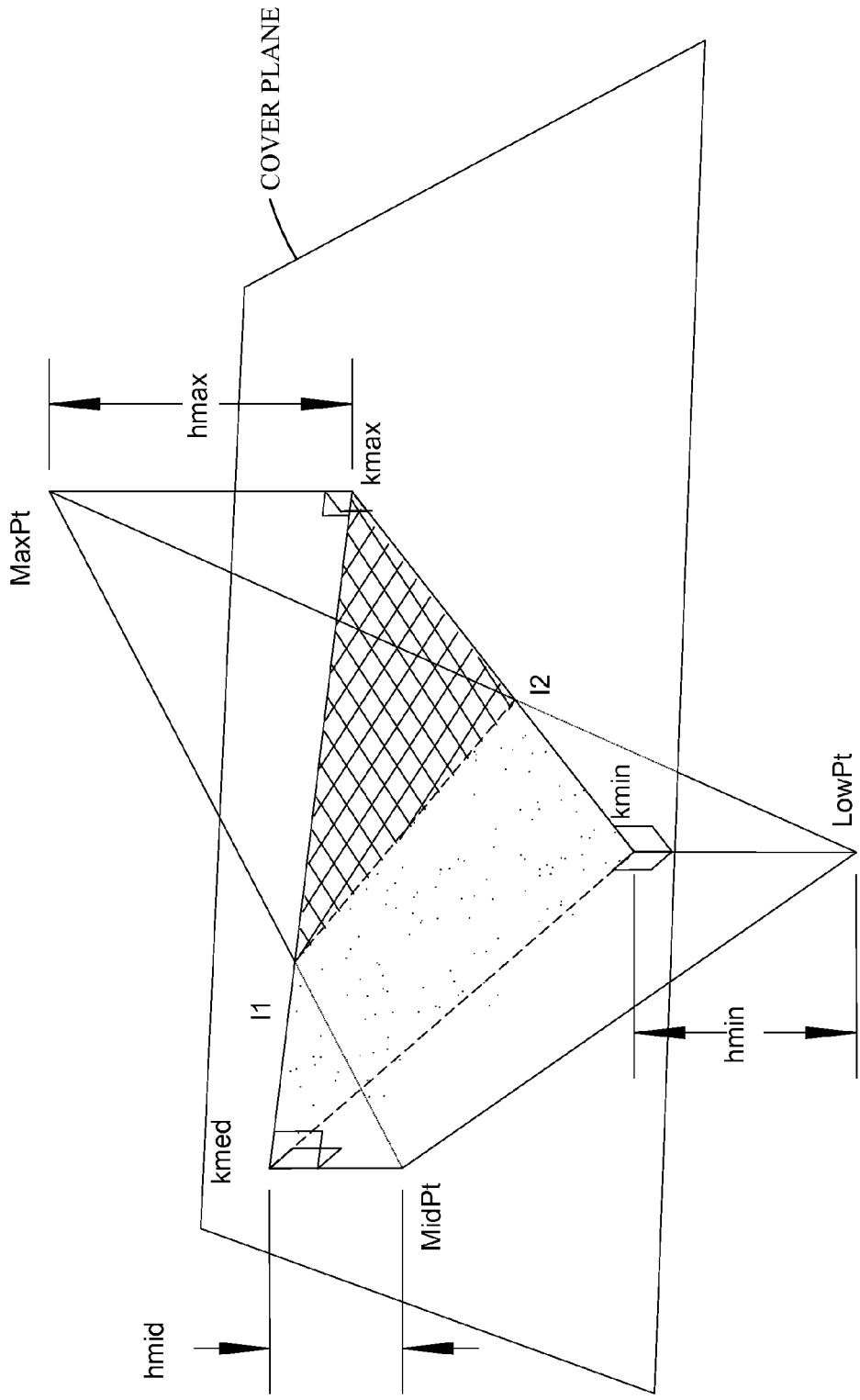
FIG. 9 is a schematic perspective of one type of triangle used to mathematically depict a portion of an absorbent structure of the present invention.

With further reference to FIG. 8, a "Cover Plane" is also determined for the absorbent structure 31. The Cover Plane represents the approximate location and orientation of the bodyside liner 26 (FIG. 2) overlaying the upper surface 41 (e.g. in contact with the peaks 51 thereof) of the absorbent article 21 when the absorbent structure is under a 0.05 psi (0.345 kPa) load, otherwise referred to herein as being "under load."

To determine the Cover Plane, a second analytical code, attached hereto as Appendix B is used to calculate the unloaded apparent, or overall thickness (indicated as TLDI in FIG. 8) of the absorbent structure 31 (e.g., from the valleys 57 of the lower surface 43 of the absorbent structure to the peaks 51 of the upper surface 41 of the absorbent structure). The Appendix B code is suitable for use with Mathematica and uses the combined (upper and lower surface 41, 43) STL data file. To determine the overall unloaded thickness of the absorbent structure 31, the center of each triangle in the combined STL data file is determined and a simple regression fit is used to fit the center points of the triangles to the equation $Z=B0+B1*X+B2*Y$. The equation defines a plane, referred to in the Appendix B code as the Best Fit Plane (not shown) for the combined upper and lower surfaces 41, 43. One skilled in the art will recognize that the Best Fit Plane for the combined STL data file is not necessarily the same as the Best Fit Plane shown in FIG. 8 for only the upper surface 41 STL data file. Next, a base point is defined on the Best Fit Plane of the combined upper and lower surfaces 41, 43 and a vector normal thereto is determined.

The distance from the center of each triangle to the Best Fit Plane of the combined STL upper and lower surfaces 41, 43 is then calculated, with positive distances being in the direction of the normal vector and negative distances being in the opposite direction of the normal vector. The unloaded thickness (TLDI) is the maximum calculated distance from the center of the triangles of the combined STL data file minus the minimum calculated distance from the center of the triangles of the combined STL data file.

To determine an overall thickness or caliper under load (TU), a bulk tester such as a Digimatic Indicator Gauge, type DF 1050E, which is commercially available from Mitutoyo Corporation of Japan, may be used. The bulk tester includes a flat base and a smooth platen connected to the indicator gauge of the tester. The platen has a diameter of about 3 inches (7.62 cm) and is capable of applying a uniform pressure of about 0.05 psi (0.345 kPa) over a 3 inch diameter (7.62 cm) portion of the absorbent structure 31. A 4 inch by 4 inch (10.16 cm by 10.16 cm) sample of the scanned absorbent structure 31 is placed on the base and the platen pressure is applied centrally of the sample such that no part of the platen overhangs the sample. Caliper measurements of the overall thickness under load are made in a room that is about 23° C. and at about 50% relative humidity. Materials that are less than 4 inches by 4 inches can be evaluated using the same technique, but require a platen that is smaller in area than the material being tested, and has a mass that will exert a pressure of 0.05 (0.345 kPa) to the material.

A new base point is then determined by shifting the base point up by an amount (indicated in FIG. 8 as "Shift Up") equal to Tmax−(TLDI−TU), where Tmax is the calculated distance between the Best Fit Plane (for the upper surface 41) and the center of the triangle spaced furthest from that Best Fit Plane in the direction of the normal vector. The new base point and the normal vector (which is normal to both the Best Fit Plane and the Cover Plane) together define the Cover Plane.

For each triangle in the upper surface 41 STL data file, the projection of the vertices of each triangle onto the Cover Plane is then calculated. With reference to FIGS. 9-12, each triangle is classified as being one of four triangle types. For triangle Type I (FIG. 9), one vertex lies above the Cover Plane and the other two vertices either lie on or lie below the Cover Plane; for triangle Type II (FIG. 10), one vertex lies above the Cover Plane, another lies on or above the Cover Plane, and the third lies below the Cover Plane; for triangle Type III (FIG. 11), at least one vertex lies below the Cover Plane and the other two either lie below the Cover Plane or lie on the Cover Plane; and for triangle Type IV (FIG. 12), all three vertices either lie on or above the Cover Plane.

In each of FIGS. 9-12, the triangle is defined by vertices indicated as LowPt, MidPt and MaxPt, with MaxPt being the vertex having the greatest, or most positive distance from the Cover Plane in the direction of the normal vector, LowPt being the vertex having the smallest, or most negative distance from the Cover Plane in the direction of the normal vector and MidPt being the remaining vertex. The designation kmax is the projection of MaxPt onto the Cover Plane, the designation kmed is the projection of MidPt onto the Cover Plane; and the designation kmin is the projection of LowPt onto the Cover Plane. The designations hmax, hmid and hmin are respective distances of the vertices from the Cover Plane, with the distance being positive if the vertex lies on the same side of the Cover Plane that the normal vector (e.g., PlaneNorm) is pointing. The line I1-I2 is the segment defined by the intersection of the triangle with the Cover Plane.

The following characteristics are then calculated:

Projected Area: The projected area corresponds to a flat area (in the horizontal plane) that would be covered by the absorbent structure 31 if the absorbent structure were laid on a flat surface. The projected area is calculated by projecting the triangles of the upper surface 41 STL data file onto the Cover Plane and summing the areas of the projected triangles. Each of the following characteristics is normalized by dividing by the projected area.

Surface Area: The surface area is the sum of the un-projected areas of all of the triangles described in the upper surface STL data file.

Figure 10:
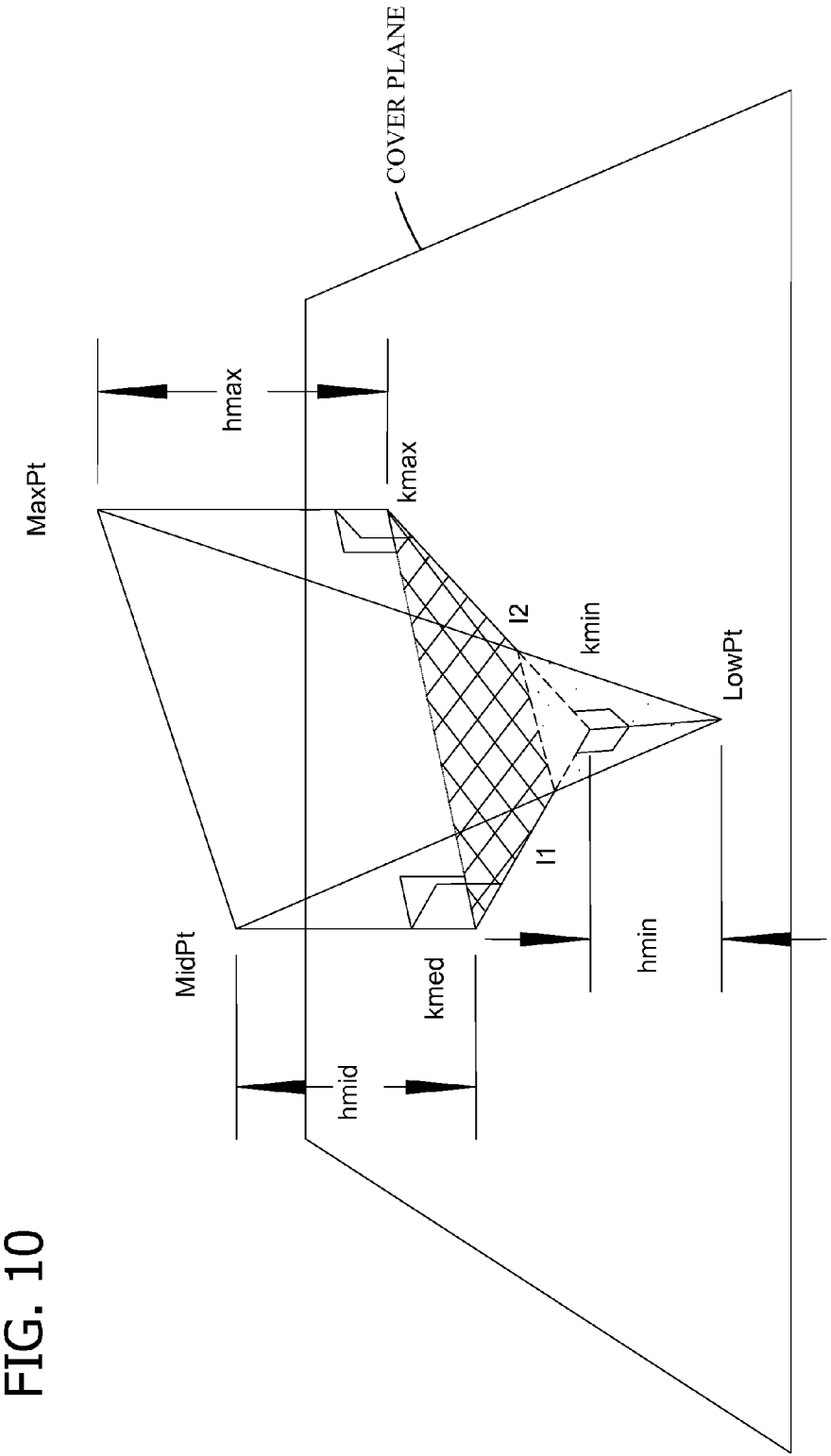
FIG. 10 is a schematic perspective of a second type of triangle used to mathematically depict a portion of an absorbent structure of the present invention.
Figure 11:
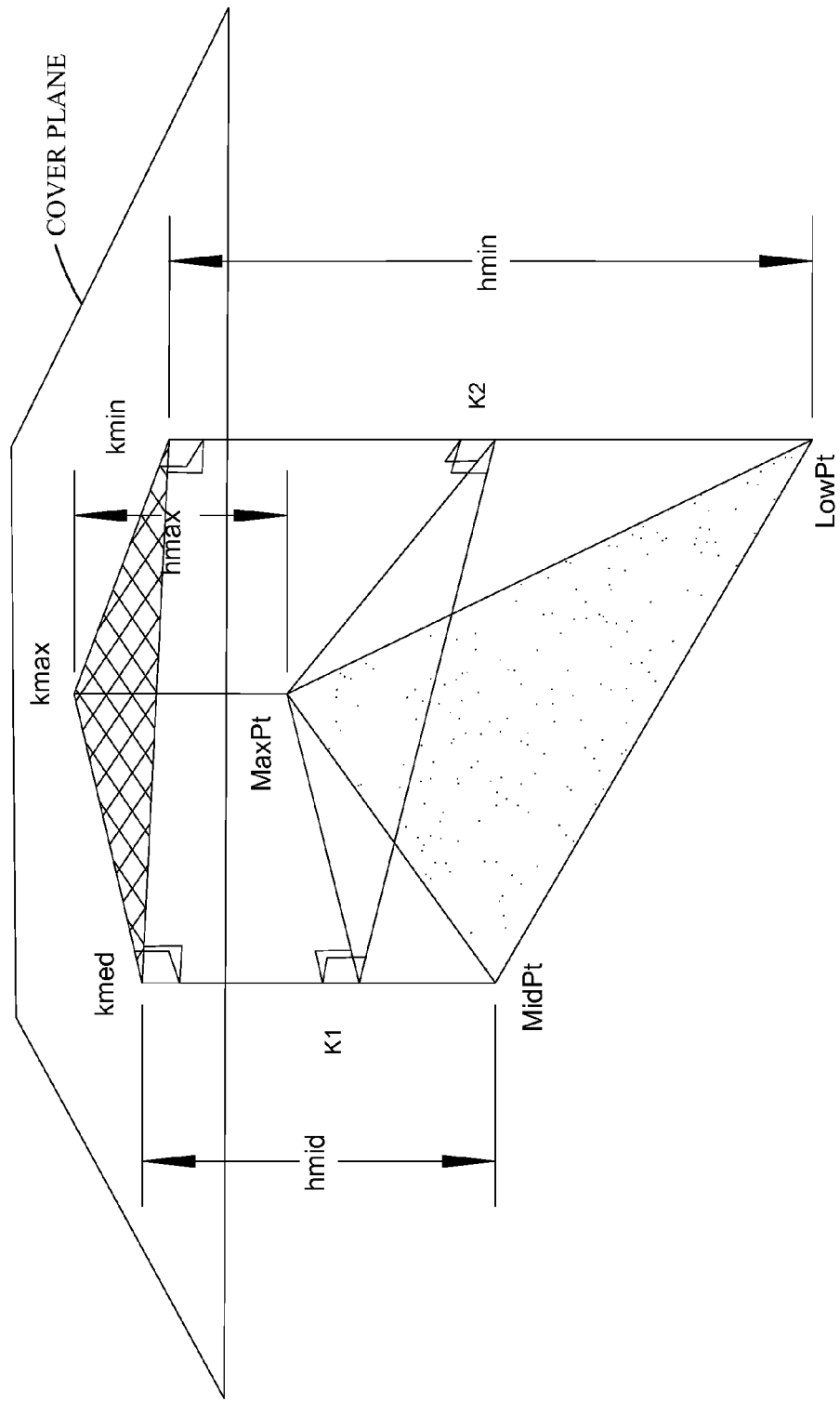
FIG. 11 is a schematic perspective of a third type of triangle used to mathematically depict a portion of an absorbent structure of the present invention.
Figure 12:
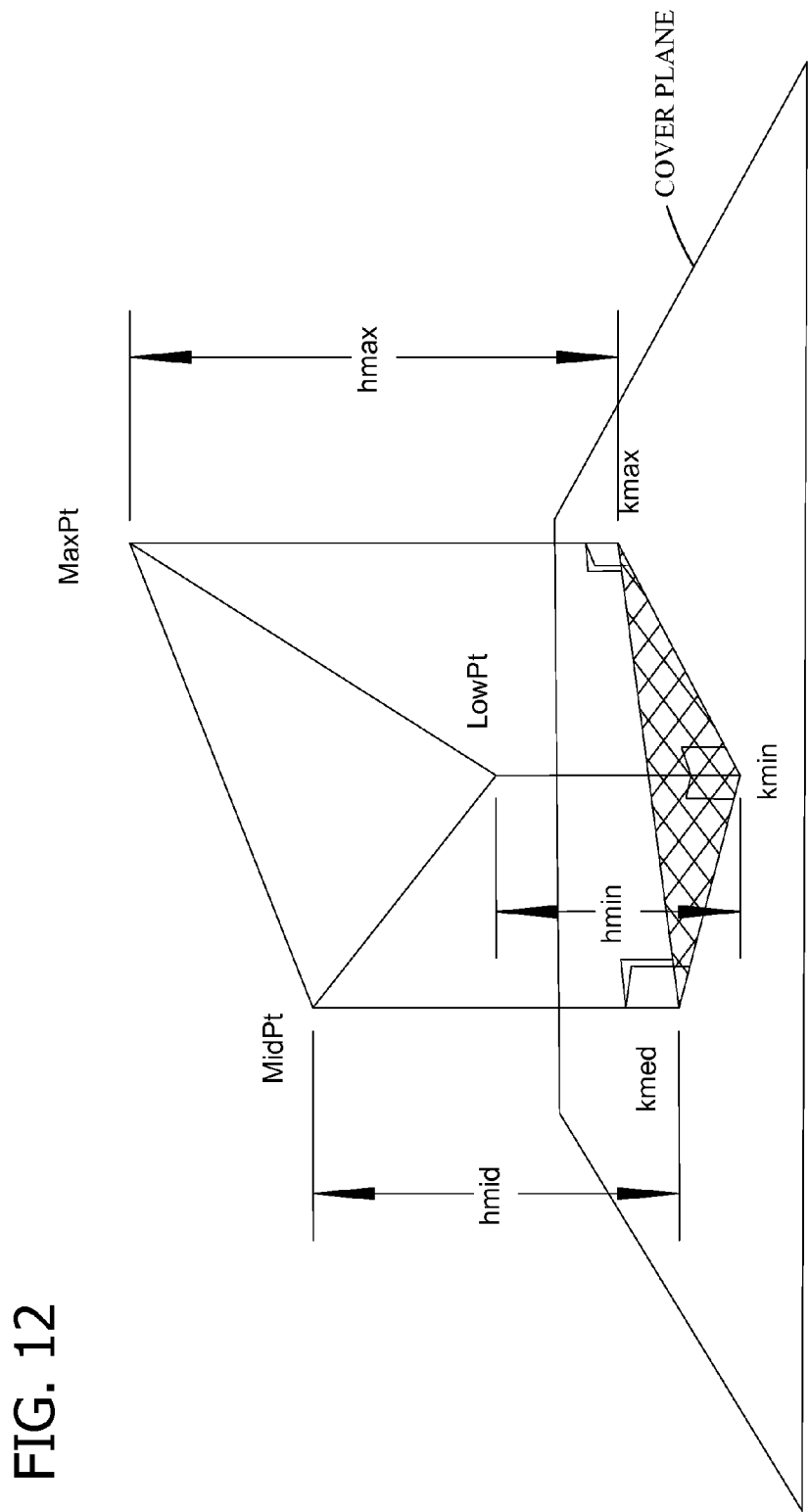
FIG. 12 is a schematic perspective of a fourth type of triangle used to mathematically depict a portion of an absorbent structure of the present invention.

Open Space Under Load: The open space under load, referred to in the Appendix A code as "volume" corresponds to the total amount of open, or air space between the liner 27 and the upper surface 41 of the absorbent structure 31 when the absorbent structure is under a 0.05 psi (0.345 kPa) load. The open space is calculated by summing the volumes defined by right triangular prisms made by each of the triangles and their respective projections onto the Cover Plane. The method for calculating the volume associated with each individual triangle depends particularly on the triangle type discussed previously. For example, the volume of a Type I triangle is the volume of the triangular pyramid defined by I1, I2, kmed and MidPt plus the volume of the rectangular pyramid defined by the points kmed, kmin, MidPt and LowPt and the apex I2. The volume of a Type II triangle is simply the volume of the triangular pyramid defined by I1, I2, kmin and LowPt. With reference to FIG. 10, the volume of a Type III triangle is calculated as the volume of a right triangular prism having a base defined by kmin, kmed and kmax and a height of hmax, plus the volume of a pyramid having a quadrilateral (K1, K2, LowPt, MidPt) as its base and the distance between MaxPt and K1 as its height. For a Type IV triangle, there is no volume between the triangle and the Cover Plane because all of the vertices of the triangle lie on or above the Cover Plane.

Contact Area Under Load: The contact area under load corresponds to the total contact area between the liner 27 and the upper surface 41 of the absorbent structure 31 when the absorbent article is under a uniform 0.05 psi (0.345 kPa) load. The contact area under load is calculated as the sum of the contact areas of each triangle with the Cover Plane, depending on the triangle type. For example, for Type I triangles, the contact area is the area of the triangle defined by I1, I2 and kmax. For Type II triangles, the contact area is the area of the quadrilateral defined by kmax, kmed, I1 and I2. There is no contact area for the Type III triangles because the triangle is completely below the Cover Plane. For Type IV triangles, the contact area is the area of the triangle defined by kmin, kmed and kmax.

Contact Perimeter Under Load: The contact perimeter under load corresponds to the total perimeter around the contact areas between the liner 27 and the upper surface 41 of the absorbent structure 31 when the absorbent article 21 is under a uniform 0.05 psi (0.345 kPa) load. The perimeter is calculated as the sum of all line segments I1-I2 defined by the intersection of the individual triangles with the Cover Plane.

Vertical Area: The vertical area corresponds to that portion of the surface area of the upper surface 41 of the absorbent structure 31 that is oriented generally in the thickness or z-direction, e.g., normal to the longitudinal and lateral axes of the absorbent structure 31. The ability of the absorbent structure 31 to resist overall thickness compression under load is at least in part due to the amount of material aligned in the direction of compression. The vertical area provides an indication of such an ability and is calculated as the sum of the components of the individual triangles of the upper surface 41 STL data file that are parallel to the vector normal to the Best Fit Plane and Cover Plane (e.g., PlaneNorm). This is equivalent to multiplying the surface area of the triangle by the length of the cross product between the PlaneNorm and the normal vector of the triangle.

In accordance with one embodiment of the present invention, the three-dimensional topography of the upper surface 41 of the absorbent structure 31 is such that the upper surface has a vertical area per projected area as determined by the Topography Analysis Method in the range of about 0.1 to about 0.5 $cm^2/cm^2$, more suitably in the range of about 0.14 to about 0.4 $cm^2/cm^2$, and even more suitably about 0.2 $cm^2/cm^2$.

The contact perimeter under load per projected area of the upper surface 41 of the absorbent structure 31 as determined by the Topography Analysis Method is suitably at least about 1 $cm/cm^2$, and more suitably at least about 1.3 $cm/cm^2$.

The upper surface 41 of the absorbent structure 31 has an open space under load per projected area as determined by the Topography Analysis Method that is suitably in the range of about 0.05 to about 1 $cm^3/cm^2$, more suitably about 0.1 to about 0.6 $cm^3/cm^2$, and even more suitably about 0.3 $cm^3/cm^2$. It is also contemplated that the open space under load per projected area of the upper surface 41 of the absorbent structure 31 as determined by the Topography Analysis Method may be greater than 1 $cm^3/cm^2$ without departing from the scope of this invention.

The total surface area of the upper surface 41 of the absorbent structure 31 per projected area as determined by the Topography Analysis Method is suitably greater than 1.00 $cm^2/cm^2$, more suitably at least about 1.05 $cm^2/cm^2$, and even more suitably at least about 1.10 $cm^2/cm^2$.

In one embodiment of a method of the present invention for making an absorbent structure 31 having a three-dimensional topography on each of the upper and lower surfaces 41, 43 of the absorbent structure, a non-woven web comprising absorbent fibers and binder material as described previously is suitably formed by conventional airlaying techniques to have generally planar (e.g., flat) upper and lower surfaces (e.g., it has no three-dimensional topography). As used herein, the term "airlaid" or "airlaying" refers to a process of producing a non-woven web wherein fibrous and/or particulate web components (e.g., the absorbent fibers and, optionally, binder material and/or superabsorbent material) are commingled in an air-stream and delivered onto a forming surface. There are a number of commercial processes available to produce air-laid absorbent structures. For example, airlaid processes are available from Danweb Corp. having offices in Risskov, Denmark, and from M&J Forming Technologies having offices in Horsens, Denmark. Suitable airlaying processes are also disclosed in U.S. Pat. Nos., 4,640,810; 4,494,278; 4,351,793 and 4,264,289.

The initial properties of the absorbent structure produce specific characteristics in the final topographical absorbent structure. For example, initially formed absorbent structures (e.g., prior to imparting topography to the upper and lower surfaces) having a range of densities can be used, such as in the range of about 0.02 g/cc to about 0.60 g/cc. Absorbent structures with lower densities tend be more formable and therefore tend to produce final topographical absorbent structures that have similar basis weights throughout the structure. In that case, the basis weight at the peaks of the upper surface tends to be generally similar to the basis weight at the valleys of the upper surface.

Higher density absorbent structures such as those having a density greater than about 0.12 g/cc tend to already have strong bonds that are formed in the airlaying process. When pressed to obtain the topographical surface properties they tend to stretch and can even tear. In these cases the basis weight and density of the structure can be changed substantially. Such shifts in basis weight can lead to shifts in local density, thereby resulting in absorbent structures with density gradients. The design of the mold plates (described later herein), the forming process method, heating method, and temperature all affect the degree of stretching and basis weight redistribution that takes place during the forming process. As an additional example, the absorbent structure is suitably initially formed to have a density in the range of about 0.2 g/cc to about 0.02 g/cc, more suitably in the range of about 0.10 g/cc to about 0.04 g/cc, and even more suitably in the range of about 0.07 g/cc to about 0.05 g/cc.

Absorbent structures 31 having different basis weights at the upper surface peaks 51 than at the upper surface valleys 53 may provide beneficial performance characteristics. For example, absorbent structures 31 having a relatively lower basis weight at the peaks 51 of the upper surface 41 than at the valleys 53 of the upper surface tend to have lower rewet and a reduced initial (first insult) intake time. As a further example, in one embodiment the absorbent structure 31 may suitably have an upper surface peak 51 basis weight to upper surface valley 53 basis weight ratio of less than about one, and more suitably less than about 0.8.

Figure 13:
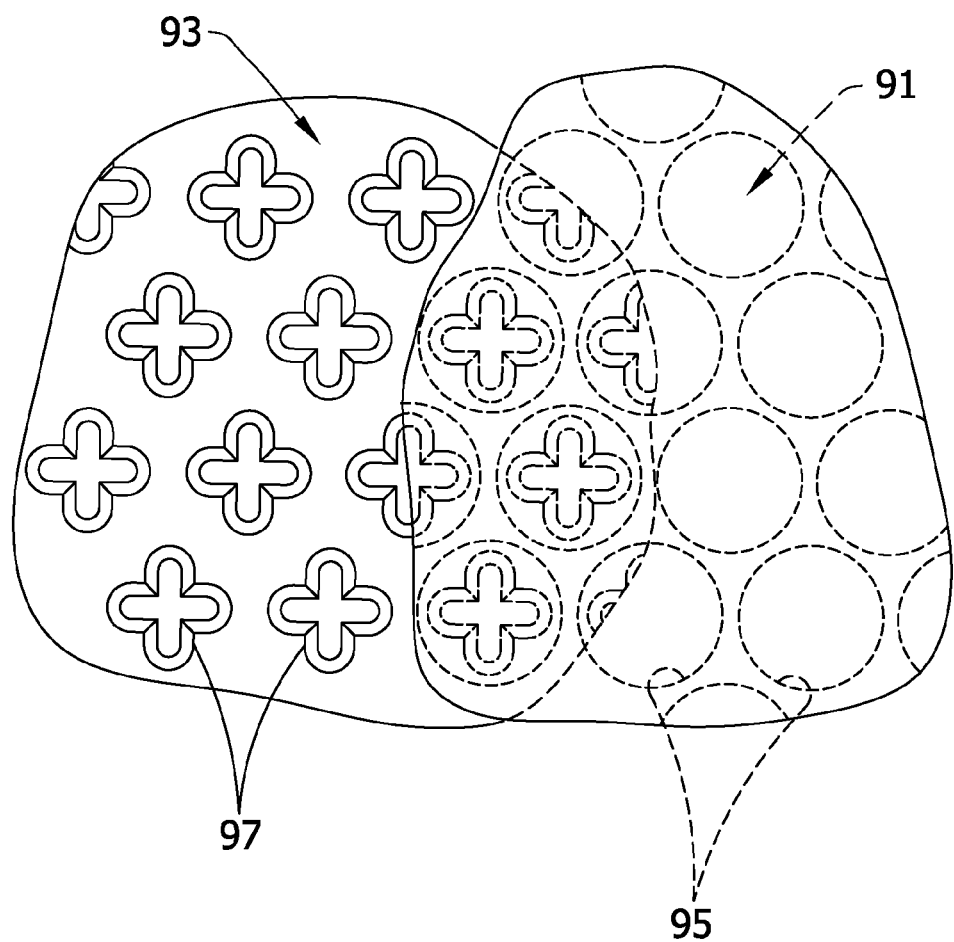
FIG. 13 is a fragmented schematic top plan of opposed mold surfaces used for forming an absorbent structure in accordance with one embodiment of a method of the present invention.

The absorbent structure 31 may alternatively be formed in another conventional manner, such as by being air-formed, co-formed, wet-layed, bonded-carded or formed by other known techniques in which fibrous and/or particulate materials are used to form a non-woven web. The absorbent structure 31 may also be a foam structure or it may be a laminate in which two or more webs are formed separately and then laminated together.

Where heat activatable binder material is present in the absorbent structure, the absorbent structure is then heated to a temperature sufficient to activate the binder material to form inter-fiber bonds within the absorbent structure, and placed between opposed mold surfaces (indicated generally at 91 and 93 in FIG. 13). For example, in one embodiment the binder material may be suitably heated to a temperature in the range of about 95° to about 200° C. As an example, where the binder fiber is T255 binder fiber commercially available from KoSa, the web is heated to at least about 230° F. (110° C.). With further reference to FIG. 13, the mold surfaces 91, 93 have respective mold patterns corresponding to the three-dimensional topographies to be imparted to the upper and lower surfaces 41, 43 of the absorbent structure 31. The heated absorbent structure 31 is placed between the mold surfaces 91, 93 while the binder fiber is activated so that the absorbent structure takes on some portion of the topography of the mold surfaces 91, 93. The material is subsequently allowed to cool below the activation temperature of the binder material to inhibit any further deformation of the absorbent structure, thereby maintaining the topography imparted to the upper and lower surfaces of the absorbent structure.

Figure 14:
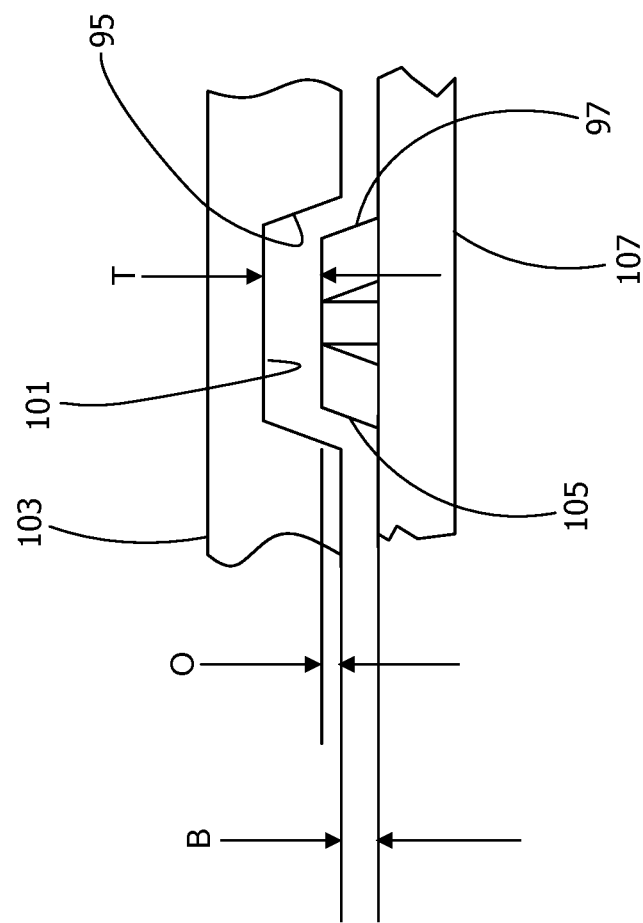
FIG. 14 is a fragmented, enlarged schematic section of the opposed mold surfaces of FIG. 13.

In the example illustrated in FIG. 13, portions of the mold surfaces 91, 93 are broken away to show the respective patterns on the mold surfaces. The upper mold surface 91 has depressions 95 formed therein which are generally circular in horizontal cross-section to impart generally circular surface features 45 to the upper surface 41 of the absorbent structure 31. The lower mold surface 93 has bumps, or pins 97 which are generally cross-shaped, or plus-shaped in horizontal cross-section to form the peaks 57 in the lower surface 43 of the absorbent structure 31. The depressions 95 in the upper mold surface 91 and the pins 97 of the lower mold surface 93 are suitably sized relative to each other to permit at least partial nesting of the pins within the depressions of the upper mold surface as shown in FIG. 14.

Figure 15B:
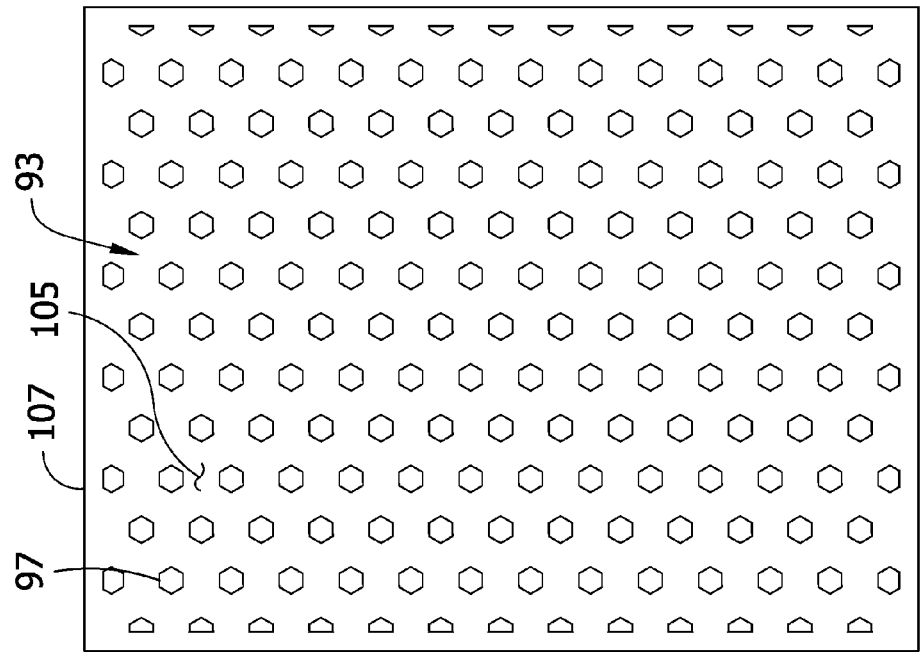
FIGS. 15A and 15B are respectively upper and lower mold plates having mold surfaces for imparting a three-dimensional topography to upper and lower surfaces of an absorbent structure of the present invention.
Figure 15A:
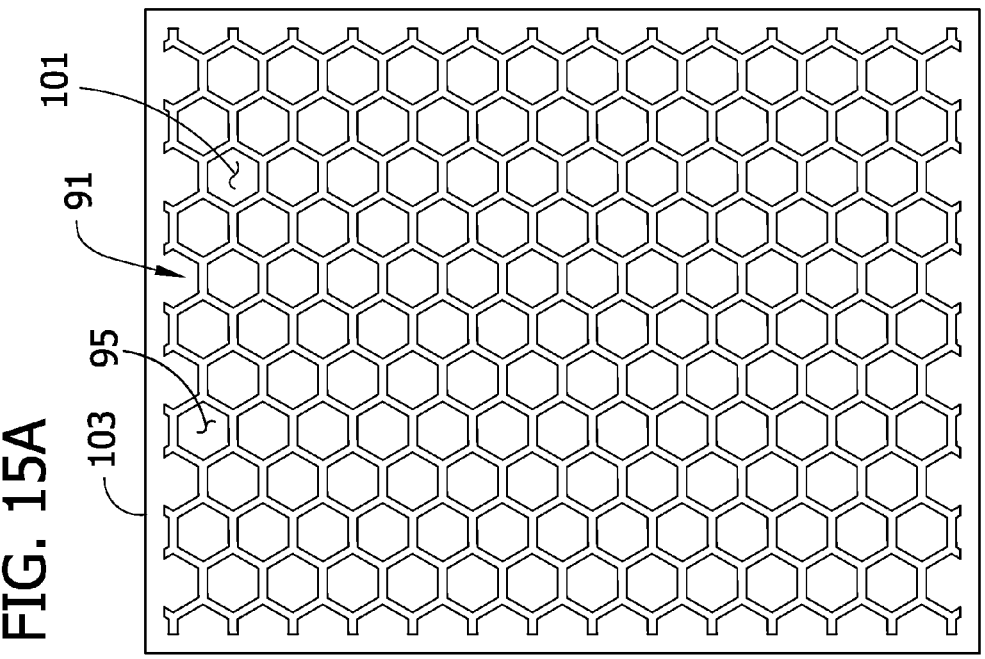

In one embodiment, such as that shown in FIGS. 15A and 15B, the opposed mold surfaces 91, 93 are respectively defined by inner surfaces 101, 105 of opposed mold plates 103, 107. The mold patterns defined by the inner surfaces 101, 105 of the mold plates 103, 107 may be non-shaped and/or otherwise substantially larger than the desired size of the absorbent structure 31 whereby the absorbent structure is cut from a larger absorbent structure after the three-dimensional topographies are imparted to the upper and lower surfaces 41, 43. Alternatively, the mold patterns may be substantially the same size as the desired absorbent structure 31 so that little or no cutting is required after molding. Additional examples of suitable mold surface patterns are shown in FIGS. 16A and 16B, 17A and 17B, and 18A and 18B and described later herein. It is understood, however, that mold surface patterns other than those shown in FIGS. 15A, 15B, 16A, 16B, 17A, 17B and 18A, 18B may be used depending on the desired three-dimensional topographies to be imparted to the upper and lower surfaces of the absorbent structure.

Figure 19:
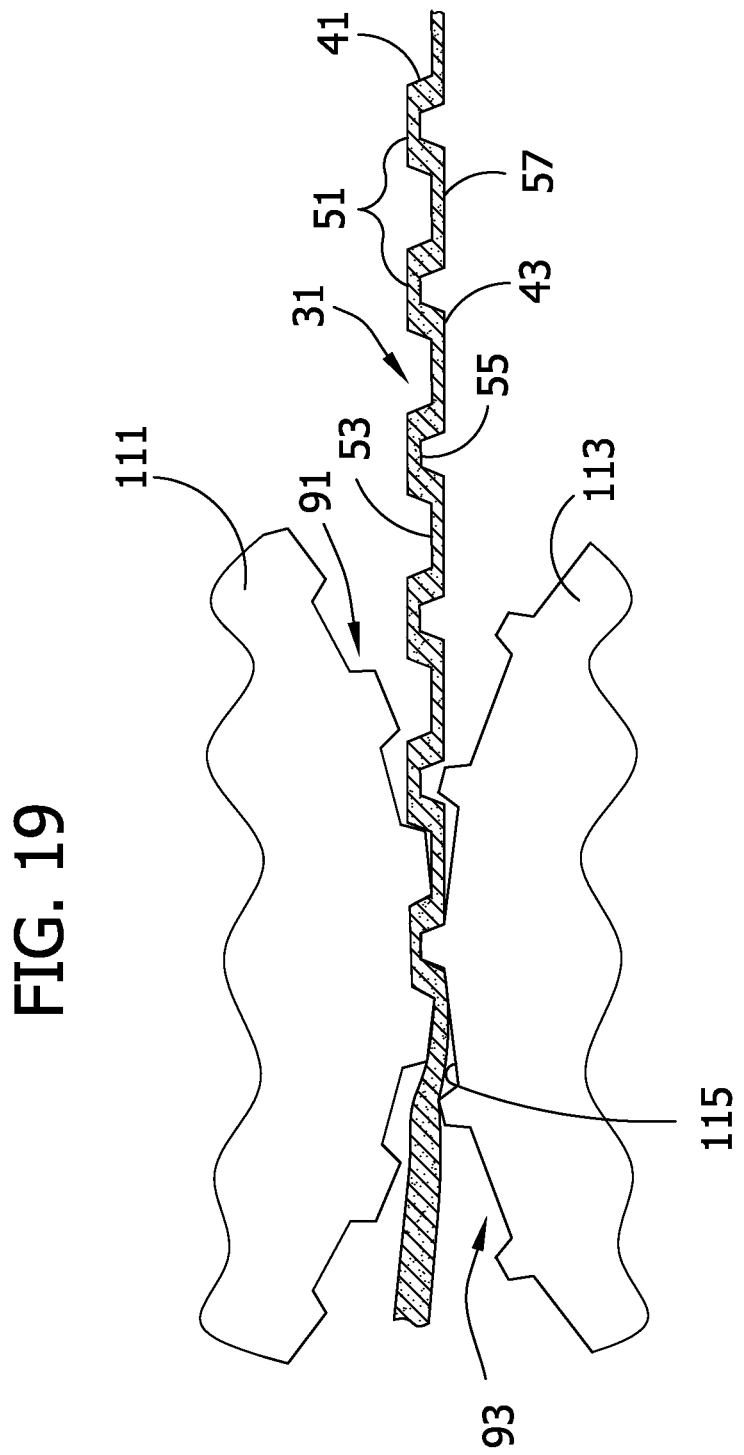
FIG. 19 is a fragmented side elevation of a pair of rolls having opposed mold surfaces formed thereon.

In an alternative embodiment shown in FIG. 19, the mold surfaces 91, 93 are formed on opposed rolls 111, 113 disposed on a commercial feminine care pad manufacturing line (not shown). Such manufacturing lines are known to those skilled in the art for assembling feminine care pads at commercial production rates from moving webs of material as the material webs are transported in a machine direction and will not be described in further detail herein except to the extent necessary to disclose the present invention. The opposed rolls 111, 113 are disposed along the manufacturing line and are arranged relative to each other to define a nip 115 through which an absorbent structure web, such as a pre-formed air-laid fibrous web, passes upon movement of the web in the machine direction. The rotational speed and phasing of the opposed rolls 111, 113 is such that the patterns of the mold surfaces 91, 93 formed on the rolls intermesh as the absorbent structure web passes through the nip 115 defined between the rolls, thereby imparting the respective three-dimensional topographies to the upper and lower surfaces 41, 43 of the absorbent structure web. The web may be cut into discrete absorbent structures 31 downstream of the rolls 111, 113 or upstream of the rolls before the three-dimensional topography is imparted to the upper and lower surfaces of the absorbent structure.

The absorbent structure web is suitably heated to activate the binder material prior to the web passing through the nip 115 between the opposed rolls 111, 113. In another embodiment, only the rolls 111, 113 are heated. In such an embodiment, the basis weight of the absorbent structure web may be redistributed as the three-dimensional topography is imparted to the upper and lower surfaces 41, 43 thereof, e.g., by redistributing, stretching and/or separating the absorbent fibers at the peaks 51, 55 and/or valleys 53, 57 of the upper and lower surfaces 41, 43 so that the basis weight of the absorbent structure 31 at the upper surface peaks is substantially less than or substantially greater than the basis weight of the absorbent structure at the upper surface valleys. In another embodiment, both the rolls 111, 113 and the absorbent structure web may be heated prior to the web entering the nip 115 formed by the rolls.

With reference back to FIG. 14, the mold surfaces 91, 93 are suitably configured relative to each other to allow a predetermined penetration depth O, or compression depth, upon urging of the mold surfaces together with the absorbent structure 31 therebetween. The penetration depth O refers to the penetration of the pins 97 of the lower mold surface 93 into the corresponding depressions 95 of the upper mold surface 91 being less than the depth at which the pins would contact the upper mold surface. The penetration depth O and the relative sizes of the pins 97 of the lower mold surface 93 and the depressions 95 of the upper mold surface 91 together define a compression thickness T at the tops of the pins (e.g., the spacing between the pins and the tops of the corresponding depressions of the upper mold surface) and a compression thickness B at the bases of the pins (e.g., the spacing between the upper mold surface at the bases of the depressions and the lower mold surface at the bases of the pins).

The compression thickness T generally defines the thickness and/or density (depending on the basis weight profile of the absorbent structure 31 prior to compression) of the absorbent structure at the peaks 51 of the upper surface 41 and the compression thickness B generally defines the thickness and/or density of the absorbent structure at the valleys 53 of the upper surface. Depending on the relative sizes of the depressions 95 of the upper mold surface 91 and the pins 97 of the lower mold surface 93, the compression thickness T and or density of the absorbent structure 31 at the peaks 51 of the upper surface 41 may be less than, equal to or greater than the compression thickness B of the absorbent structure at the valleys 53 of the upper surface without departing from the scope of this invention.

Experiment

An experiment was conducted to determine the intake and rewet performance characteristics of absorbent structures formed in accordance with the present invention. In the experiment, absorbent structures 31 were formed from about 90% by weight fluff pulp commercially available from Weyerhauser of Federal Way, Wash., U.S.A. as model designation NF-401 and about 10% by weight bicomponent binder fiber commercially available from KoSa of Houston, Tex., U.S.A. as model designation T255. The absorbent structures 31 were initially airlaid by a suitable airlaying process as described previously and were sized or otherwise cut to approximately 8 inches by 10.5 inches. One set of absorbent structures 31 was formed to have a generally uniform basis weight of about 120 grams per square meter (gsm) and another set was formed to have a generally uniform basis weight of about 225 gsm. The actual basis weight was suitably within +/−5% of the target basis weight. The absorbent structures were formed to have an average density (prior to processing that created the surface topography) in the range of about 0.054 g/cc to about 0.066 g/cc.

Mold plates 103, 107 used to form the three-dimensional topography on the upper and lower surfaces 41, 43 of certain ones of the absorbent structures included the mold plates shown in FIGS. 15A, 15B, 16A, 16B, and 17A, 17B, each measuring about 5 inches by about 20 inches (12.7 cm by about 50.8 cm) and the mold plates shown in FIGS. 18A, 18B, each measuring about 8.5 inches by 11 inches (about 21.6 cm by 27.9 cm). The mold plates 103, 107 were placed in a heated platen press (not shown), such as that available from Carver Press of Wabash, Ind., U.S.A., under model #3895 4D10A00. The surface area of the outer (flat) surface of one of the mold plates 103 was measured and the pressure required to apply approximately 6,500 psi (44,817.5 kPa) was calculated. For example, the flat surface area of the mold plate 103 of FIG. 18a was about 600 cm$^2$, requiring a platen pressure of about 10,000 psi (68,950 kPa). The platen press was pre-heated to about 230° F. (110° C.).

After the platen press was heated the mold plates 103, 107 were heated by pressing them in the platen press for 42 seconds without any material. Additional pre-heating of the plates 103, 107 was done on any plate that had not recently been used. The absorbent structure as initially formed was placed centrally on the lower mold plate 107 so that approximately 0.25 inches (0.64 cm) of the lower plate extended out beyond the ends and side edges of the absorbent structure. The upper mold plate 103 was then placed over the lower mold plate 107, with the exposed portion of the lower mold plate used to align the plates. The exposed portion of the lower mold plate 107 and the upper mold plate 103 were partially pressed into each other to ensure proper alignment of the plates. The required pressure was then applied to the mold plates 103, 107 to thereby compress the absorbent structure 31 and, as described previously, to impart the mold surface patterns to the upper and lower surfaces 41, 43 of the absorbent structure. The plates were pressed together for 42 seconds, and then opened. The mold plates and material were removed from the press. The top plate was carefully removed from the material to prevent deformation of the material before the binder material had sufficiently cooled.

Five different mold surface patterns were used, one to impart a compressed but otherwise flat (non-three-dimensional) topography to the upper and lower surfaces 41, 43 of the absorbent structure 31 and four different patterns to impart four different three-dimensional topographies to the upper and lower surfaces of the absorbent structure.

1) FIGS. 15A and 15B illustrate mold plates 103, 107 having mold surfaces 91, 93 patterned to impart a three-dimensional topography to the upper and lower surfaces 41, 43 wherein the peaks 51, 55 of the upper and lower surfaces are generally hexagonal in horizontal cross-section. The hexagon shaped depressions 95 in the upper mold plate 103 (FIG. 15A) are spaced center to center from each other a distance of about 2.0 cm, as are the pins 97 of the lower mold plate 107. The sides of the hexagonal pins 97 (at the top thereof) are each about 5 mm and the height of each pin is about 0.3 cm. The mold plates 103, 107 are configured to impart a feature density to the upper surface 41 of the absorbent structure 41 of about 0.29 per square centimeter of projected area.

Figure 16B:
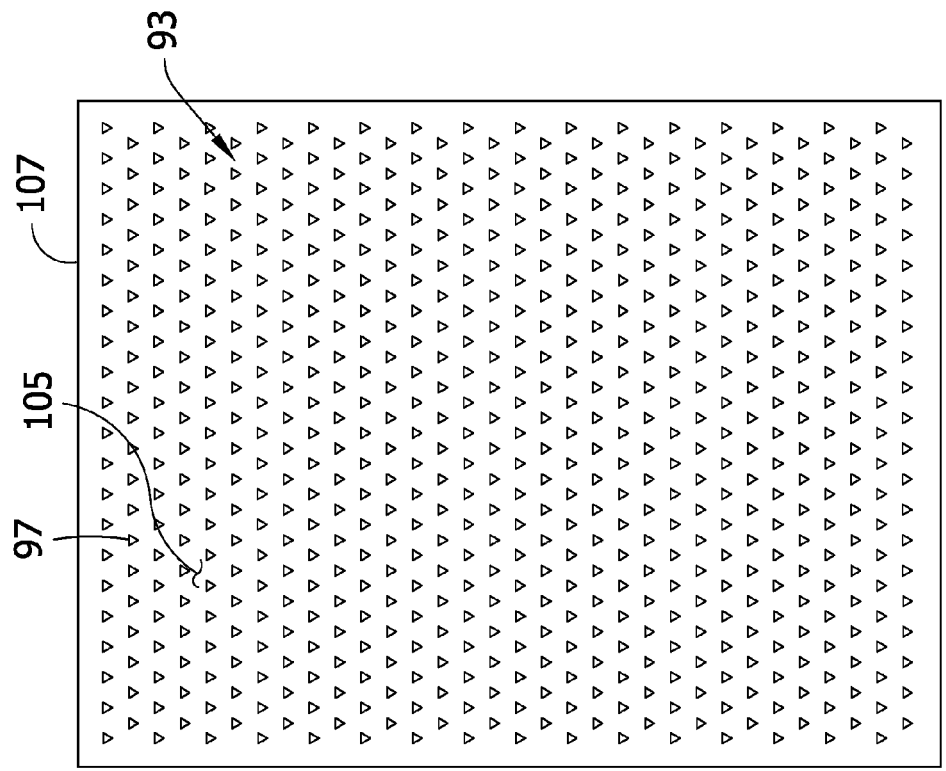
FIGS. 16A and 16B are a second embodiment of respective upper and lower mold plates having mold surfaces for imparting a three-dimensional topography to upper and lower surfaces of an absorbent structure of the present invention.
Figure 16A:
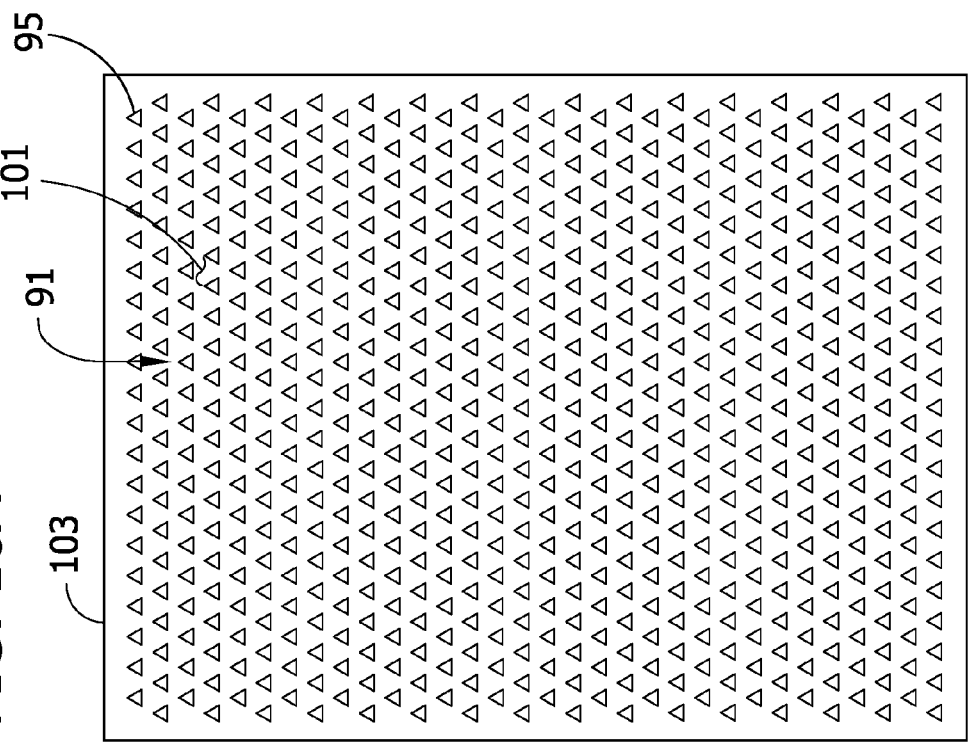

2) FIGS. 16A and 16B illustrate mold plates 103, 107 having mold surfaces 91, 93 patterned to impart a three-dimensional topography to the upper and lower surfaces 41, 43 wherein the peaks 51, 55 of the upper and lower surfaces are generally triangular in horizontal cross-section. The triangular shaped depressions 95 in the upper mold plate 103 (FIG. 16A) are equilateral triangles spaced center to center from each other a distance of about 0.9 cm, as are the triangular shaped pins 97 of the lower mold plate 107. Each of the triangular pins 97 has side lengths (at the top thereof) of about 5 mm. The height of each triangular pin is about 0.3 cm. The mold plates 103, 107 are configured to impart provide a surface feature density on the upper surface 41 of the absorbent structure 41 of about 1.18 per square centimeter of projected area.

Figure 17B:
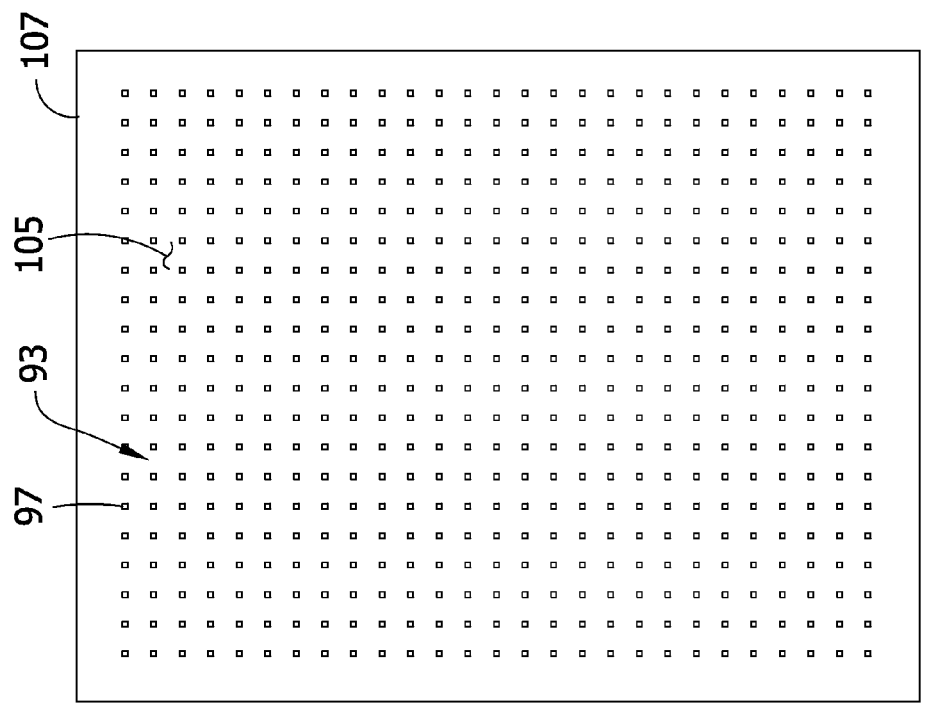
FIGS. 17A and 17B are a third embodiment of respective upper and lower mold plates having mold surfaces for imparting a three-dimensional topography to upper and lower surfaces of an absorbent structure of the present invention.
Figure 17A:
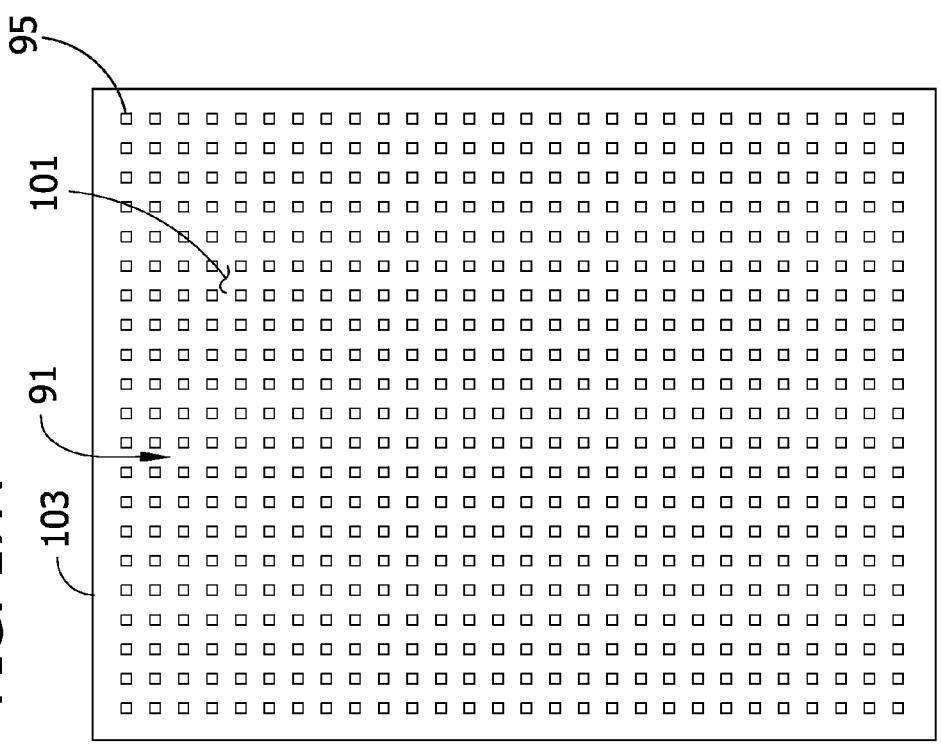

3) FIGS. 17A and 17B illustrate mold plates 103, 107 having mold surfaces 91, 93 patterned to impart a three-dimensional topography to the upper and lower surfaces 41, 43 wherein the peaks 51, 55 of the upper and lower surfaces are generally square in horizontal cross-section. The square depressions 95 in the upper mold plate 103 (FIG. 17A) are spaced center to center from each other a distance of about 0.95 cm, as are the square pins 97 of the lower mold plate 107. The square pins 97 are sized to have side lengths (at the top thereof) of about 3.5 mm. The height of each pin 97 is about 0.3 cm. The mold plates 103, 107 are configured provide a surface feature density on the upper surface 41 of the absorbent structure 41 of about 2.2 per square centimeter of projected area.

4) FIGS. 18A and 18B illustrate mold plates having mold surfaces configured to impart a three-dimensional topography to the upper and lower surfaces 41, 43 wherein some of the peaks 51, 55 and valleys 53, 57 of the upper and lower surfaces 41, 43 are generally serpentine and others are generally circular in horizontal cross-section. The serpentine channels formed in the upper mold plate are generally about 0.46 cm in cross-section and provide a surface feature density of about 0.79 per square cm of projected area. The width of the bond pattern on the upper surface of the mold plate was 0.8 mm. The depth of the bond pattern was 0.3 cm. The serpentine pattern had a portion that was approximately a sine wave with a wavelength of 1.75 cm and an amplitude of 0.24 cm. The bottom mold plate also had a pattern depth of 0.3 cm and a bond pattern width of 0.8 mm at its upper surface. The sinusoidal wave portion of the pattern had an amplitude of 0.24 cm and wavelength of 1.75 cm. The circular portion had a diameter of 1.0 mm.

Figure 20:
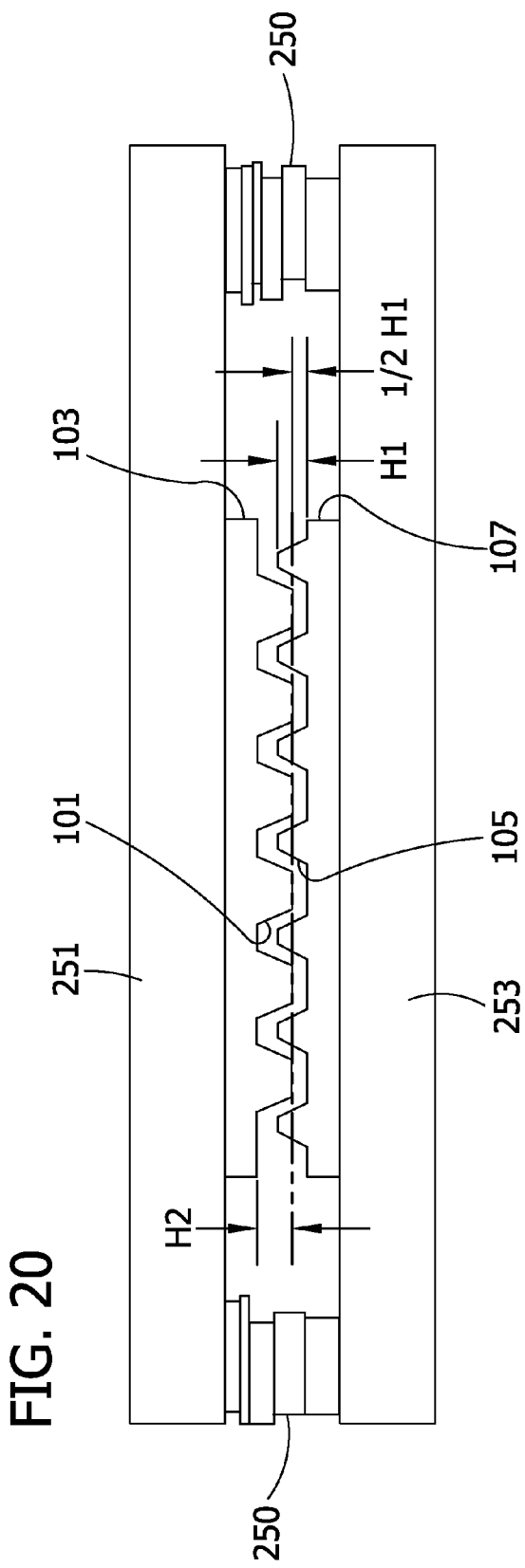
FIG. 20 is a schematic of opposed mold surfaces intermeshed with each other to one-half of the full penetration depth thereof.

The absorbent structures were compressed between the mold plates 103, 107 to either a full penetration depth O (FIG. 14) or to one-half of the penetration depth for a duration of 42 seconds. With reference to FIG. 20, to achieve a one-half penetration depth, the depth of the mold surface pattern on each of the upper and lower mold plates 103, 107 of a respective pair of plates was measured to determine which plate had the smallest depth (the smallest depth being labeled as H1 and the depth of the other plate being H2 in FIG. 20). This depth (H1) was then divided by two. Metal shim stock 250 was placed between upper and lower platens, respectively designated 251 and 253 in FIG. 20. The shim stock thickness was chosen so that when the plates 103, 107 were urged together by the platens 251, 253, penetration of the pins on the mold surface of the plate opposite the plate having the smallest depth was limited to one-half the smallest penetration depth (H1). Absorbent structures made at "full" penetration depth were made without shim stock to limit the penetration of one plate into another. The full pressure of the press is exerted onto the material to impart the topography into the web.

The various absorbent structures 31 formed for testing are set forth in the table of FIG. 24. Two control absorbent structures 31 (one having a gsm of about 120 and the other having a gsm of about 225) were not further processed after air-laying (e.g., they remained uncompressed and had no three-dimensional topography).

For each absorbent structure 31, 4 inch by 4 inch (10.16 cm by 10.16 cm) samples were cut therefrom, taking care not to stretch or otherwise distort the material. Samples of each absorbent structure were split randomly into two sets. Samples from one set were used in to measure their intake and rewet properties. Samples from the second set were used to measure the overall thickness of the sample for later use with the Topography Analysis Method. These samples were sent to Laser Design Inc. of Minneapolis, Minn. for scanning. FIGS. 21 and 22 illustrate a sample holder, generally indicated at 201, for holding the absorbent structure sample during scanning. The sample holder 201 generally comprises a pair of opposed, acrylic plates 203a, 203b, each having dimensions of about 13.5 cm by 13.5 cm and a central, generally octagonal opening 205. Bolt holes 206 (four of them) are disposed generally adjacent the corners of each plate 203a, 203b to accommodate a bolt 207 and a coil spring 209 axially mounted on the bolt between the plates. A wing nut 210 is threadably received on each bolt 207. A set of four pin holes 211 is also formed in each plate 203a, 203b to receive retaining pins 213 therethrough for purposes which will be described. At least one insert (not shown) is sized for being received in the octagonal opening 205 of the lower plate 203b. Alternate sample holding fixtures can be designed to hold materials that are smaller without departing from this general approach. Fixtures must be capable of holding the material in a flat state without movement and allow simultaneous unobstructed viewing of both sides of the material.

To scan the absorbent structure sample, the lower plate 203b of the sample holder 201 was placed face down on a flat surface with the bolts 207 extending up through the bolt holes 206 in the lower plate and the insert was inserted into the central octagonal opening 205. The absorbent structure sample was centrally placed on the lower plate 203b. The springs 209 were then axially mounted on the bolts 207 and the upper plate 203a was placed over the absorbent structure sample with the bolts passing outward through the bolt holes 206 in the upper plate. The wing nuts were threaded onto the bolts 207 and tightened until the plates 203a, 203b just touched the upper and lower surfaces 41, 43 of the absorbent structure sample. The retaining pins 213 were inserted through the pin holes 211 in the upper plate 203a and into the absorbent structure sample to retain the sample in the holder 201. The holder 201 (with the sample retained therein) was then lifted off of the flat surface, leaving the insert, and positioned on the scanning device for scanning. Each of the upper and lower surfaces 41, 43 of the sample was then scanned to derive point cloud data. The point cloud data was converted into triangle data which was then converted into the upper surface (or "front") STL data file, and the combined (upper and lower surface) STL data file.

The STL data files corresponding to each of the samples were then subjected to the Topography Analysis Method set forth herein to determine various upper surface characteristics of the absorbent structures. More particularly, three subsets of each STL data file, each subset corresponding to either an approximately 1 inch by 1 inch (2.54 cm by 2.54 cm) square portion of the absorbent structure sample or to a square portion of the absorbent structure sample sized sufficient to contain at least one and a half full repeats of the upper surface topography pattern in both the longitudinal and lateral directions, were generated. The subsets were analyzed using the Topography Analysis Method and the results were averaged to determine the projected area, total surface area, vertical area, contact area under load, perimeter under load and open space under load defined by the upper surface of each sample. The results are tabulated in the table shown in FIG. 24, with the total surface area, vertical area, contact area under load, perimeter under load and open space under load normalized by dividing by the projected area.

Additional 4 inch by 4 inch (10.16 cm by 10.16 cm) absorbent structure samples of the subject absorbent structures 31 were used to perform an Intake and Rewet Test as set forth later herein to determine the liquid intake and rewet properties of the absorbent structures. Intake measures the amount of time needed for a liquid, e.g., menses, to be taken into the absorbent structure 31 upon repeated insults thereof. Rewet measures the amount of liquid, e.g. menses, that flows back to the outer surface of the absorbent structure 31 (after taking in at least three insults) upon the application of a compressive pressure to the absorbent structure. The results of the Intake and Rewet Test are provided in the table of FIG. 25.

Typically, there is an inverse relationship between intake results and rewet results as evidenced by comparing the materials with the flat topography at half and full depth in the table of FIG. 25. The one-half penetration depth flat samples had better intake times (faster intake) and worse rewet (higher rewet) than the flat samples with the full penetration depth compression (e.g., having higher density). However, absorbent structures formed in accordance with the present invention simultaneously improved both intake and rewet.

Results from this experiment were used to generate a linear regression model that used the topographical features of the upper surface of the absorbent structure samples as the independent variables, and the intake/rewet results as the dependent variables. Simple regression analysis was done to verify the independence of the topographical features. A relevant statistical model was found for each triple gush insult and for the rewet. The statistics for the models are as follows:

| Predicted Property | Adjusted R-Square for model | Likelihood the model is actually a constant. |
|---|---|---|
| $1^{st}$ intake | 0.41 | 0.01 |
| $2^{nd}$ intake | 0.77 | <0.001 |
| $3^{rd}$ intake | 0.69 | 0.002 |
| Rewet | 0.79 | <0.001 |

Thus, the topographical properties of the upper surface of the absorbent structure as determined by the Topography Analysis Method are meaningful drivers for controlling liquid movement, and in particular intake and rewet, in absorbent structures. Using this information it is possible to design absorbent structures having surface topographies that provide desired absorbent properties.

Intake and Rewet Test

The Intake and Rewet Test determines differences between absorbent structures designed for absorption of menses in the rate of intake and the amount of flow back to the surface (e.g., rewet) of the absorbent structure under pressure when at most three insults of menses simulant are applied to the absorbent structure, with time allowed for the simulant to distribute within the absorbent structure between insults.

For each of the tests done in the experiment, one of the absorbent structure samples described previously and set forth in the table of FIG. 24 was used as the upper layer in a two layer system. The lower layer was of equal size relative to the upper layer and comprised a 225 gsm airlaid material made with 75% NF-416 fluff pulp from Weyerhaeuser, 10% T-255 bicomponent binder fiber from KoSa, and 15% SXM-9543 Superabsorbent particles from Stockhausen. Additionally a 0.6 osy (20 gsm) spunbond fabric was used as a liner overlaying the upper layer and contained 0.45% Ahcovel surfactant.

Figure 23A:
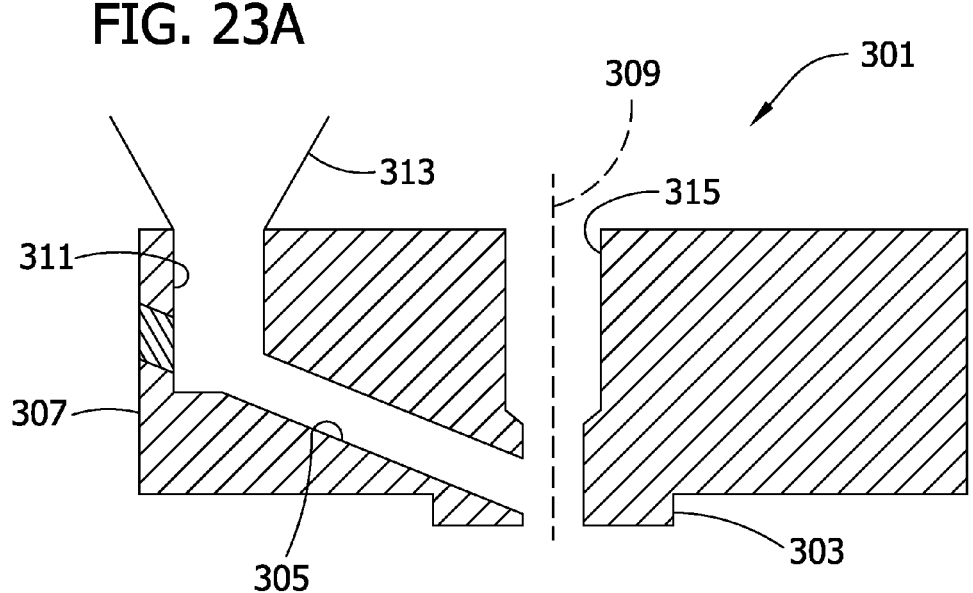
FIG. 23A is a vertical cross-section of a rate block for conducting an Intake and Rewet Test.
Figure 23B:
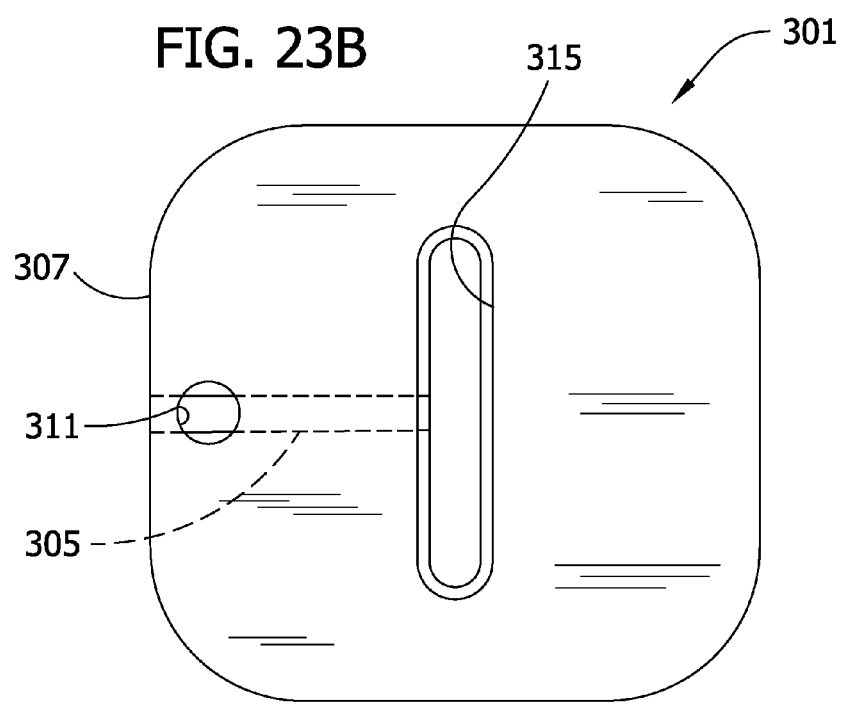
FIG. 23B is a top plan view of the rate block of FIG. 23A.

Equipment Needed:
Acrylic rate block (FIGS. 23A and 23B)
5 ml capacity pipettor (e.g., the pipetman P5000 available from Gilson Inc, Middleton, Wis.)
Small beaker;
Menses simulant warmed in bath for 10 minutes to 26° C.;
Blotter paper—Verigood, White cut to about 7.6 cm by 12.7 cm. Two sheets per absorbent structure being tested;
Small spatula or stirrer;
5 ml funnels for rate block;
Stop watch
One or two timers
Gauze or paper towels for clean up
10% CHLOROX solution
Electronic balance accurate to 0.01 grams
Test Stand (FIGS. 26A and 26B)
The rate block (shown in FIGS. 23A and 23B and indicated generally at 301) is made of clear acrylic and is 3 inches (76.2 mm) wide by 2.87 inches (72.9 mm) deep (into the page) by 1.25 inches (31.8 mm) in height. The rate block 301 includes a central portion 303 projecting out from the bottom of the block and having a height of about 0.125 inches (3.2 mm) and a width of about 0.886 inches (22.5 mm). The rate block 301 has a channel 305 with an inside diameter of 0.188 inches (4.8 mm) that extends diagonally downward from one side 307 of the rate block to a center line 309 thereof at an angle of about 22 degrees from horizontal. The channel 305 may be made by drilling the appropriately sized hole from the side 307 of the rate block 301 at the proper angle beginning at a point 0.716 inches (18.2 mm) above the bottom of the rate block; provided, however, that the starting point of the drill hole in the side must be subsequently plugged so that menses simulant will not escape therefrom.

A top hole 311 has a diameter of about 0.312 inches (7.9 mm), and a depth of 0.625 inches (15.9 mm) so that it intersects the channel 305. The top hole 311 is centered 0.28 inches (7.1 mm) from the side 307 and is sized for receiving a funnel 313 therein. A center bore 315 allows viewing of the progression of the menses simulant as it is taken into the absorbent structure and is ovate in cross-section. The center bore 315 is centered width-wise on the rate block 301 and has a bottom hole width of 0.315 inches (8 mm) and enlarges in size from the bottom of the rate block, for ease of viewing, to a width of 0.395 inches (10 mm). The top hole 311 and center hole 315 may also be drilled into the rate block 301. The rate block as an average weight of 161.9 grams and therefore exerts a pressure of 0.62 kPa over an area of 25.6 cm$^2$.

The test stand (shown in FIGS. 26A and 26B and indicated generally at 401) comprises a 7.75 inch by 10 inch (19.7 cm by 25.4 cm) platen 403 supported by a pneumatic cylinder 405 and piston 407 below a fixed plate 409. A hot water bottle 411 sized approximately 7.5 inches by about 10.75 inches and filled with water is seated on the platen 403 for supporting the sample to be tested. The piston 407 is moveable via pneumatic pressure within the cylinder 405 to raise the platen 403 (and the hot water bottle 411 and sample supported by the platen) toward the fixed plate 409 to generally squeeze the sample between the hot water bottle and the fixed plate 409. The pressure within the cylinder 405 is regulated by a suitable pressure regulator (not shown). The hot water bottle 411 evenly distributes pressure evenly across the test sample, which may or may not have the same height in the center than it does at its edges. For that reason the hot water bottle 411 must be sufficiently filled to allow equal redistribution of the pressure.

Menses Simulant

The menses simulant used for the Intake/Rewet Test is intended to simulate menses in its liquid handling properties. The simulant is made by Cocalico Biologicals, Inc. of Reamstown, Pa., U.S.A. and is composes of swine blood and chicken egg whites. It has a Hematocrit value of 30%±2% and a bioburden of <250 CFU/ml. Such a menses simulant is known to those skilled in the art and is described in U.S. Pat. No. 5,883,231, which is incorporated herein by reference. Established guidelines for handling blood-borne pathogens, including personal protection, handling and post-use sterilization must be followed when working with the swine blood based menses simulant.

Prior to using the menses simulant for the Intake/Rewet Test, the simulant is removed from the refrigerator and placed in a water bath for 10 minutes at 26° C. Before cutting open the bag for use, the bag is massaged between hands for a few minutes to mix the simulant, which will have separated in the bag. The bag tubing is then cut and the amount of simulant needed for testing is poured into the small beaker. The simulant in the beaker is stirred slowly with the small spatula to mix thoroughly.

Test Procedure

The two blotters are weighed dry.

The rate block 301 is aligned such that the long direction of the central portion 303 is aligned with what would be the length direction of a product containing the material. This is commonly the MD of the material. The rate block 301 is then placed in the center of the sample to be tested and the sample is insulted with 2.0±0.01 ml of the menses simulant from the pipettor into the funnel 313. The stopwatch and timer are started simultaneously when the first insult reaches the test material. The time needed for the simulant to be taken into the absorbent structure sample is recorded as the first intake time (e.g., in seconds). The stopwatch is started at the beginning of the insult and stopped when the fluid has been absorbed below the liner. The timer remains on and is used to indicate when subsequent insults are completed. If a ring of simulant remains around the inside of the rate block 301, this should be ignored.

When the timer indicates nine minutes have elapsed since the start of the test, a second insult of 2±0.01 ml of menses simulant is applied to the absorbent structure sample and the time needed to taken in the simulant is recorded as the second intake time. When the timer indicates eighteen minutes have elapsed since the start of the test, the procedure is repeated for a third insult to measure and record a third intake time. In the event the intake time is greater than 9 minutes the test is stopped for that sample.

When the timer indicates twenty-seven minutes have elapsed since the start of the test, the rate block 301 is removed from the sample and the two dry, pre-weighed blotters are placed on top of the sample. The blotter papers are centered over the center of the wetted area. The sample and blotters are together placed on the hot water bottle 411 in the test stand 401 and a uniform 1.0 psi (6.9 kPa) pressure is applied to the blotter paper/absorbent structure system via the pneumatic cylinder 405 and piston 407 for a period of 180 seconds. The blotters are then removed and weighed. The amount of rewet, in grams weight, is the difference between the weight of the blotters when wet and the weight of the blotters when dry.

The Intake and Rewet Test is conducted on five absorbent structure samples and the results are averaged to obtain the intake times and rewet for a particular absorbent structure.

When multiple lots of menses simulant are used, each sample to be tested is randomly assigned to a particular lot of simulant.

While the absorbent article (e.g., the pad 21) is shown and described herein as including only an absorbent structure 31 disposed between the liner 27 and the outer cover 29, it is understood that other material webs or layers may be disposed between the liner and the outer cover, such as between the absorbent structure and the outer cover or between the absorbent structure and the liner. For example, one such layer is disclosed in co-assigned U.S. patent application entitled Multilayer Absorbent Article, filed by Fell et al. and referred to therein as a shaping layer.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description shall be interpreted as illustrative and not in a limiting sense.

APPENDIX A

■ (*Load the function libraries *)
   <<Graphics`Graphics`
   <<LinearAlgebra`Orthogonalization`
■ (*Define New Functions*)
  (*This is the function that determines
    the area of a triangle defined by points AB,BP,CP*)
  SurfaceArea=Compile[
    {{AP, _Real, 1}, {BP, _Real, 1}, {CP, _Real, 1}}, If[({AP≠BP) && (BP≠CP),
      ½Sqrt[(AP−BP)·(AP−BP)]Sqrt[((−AP+CP)·(−AP+CP)−((AP−BP)·(AP−BP)−
        (BP−CP)·(BP−CP)+(−AP+CP)·(−AP+CP))$^2$/(4 (AP−BP)·(AP−BP)))], 0]];
  (*This is the function that defines the location
    of the point projected from P1 to the plane defined*)
  (* by the base point PlaneBase and the normal vector PlaneNorm*)
  ProjectPoint=Compile[{{PlaneBase, _Real, 1), {PlaneNorm, _Real, 1}, {P1, _Real, 1}},
    P1−PlaneNorm*((P1−PlaneBase)·PlaneNorm)];
  (*This function defines the area of a "Shadow" of a triangle projected onto a plane*)
  ProjectedArea=Compile[{{PlaneBase, _Real, 1, {PlaneNorm, _Real, 1}, {P1, _Real, 1},
    {P2, _Real, 1}, {P3, _Real, 1}}, AP=ProjectPoint[PlaneBase, PlaneNorm, P1];
    BP=ProjectPoint[PlaneBase, PlaneNorm, P2];
    CP=ProjectPoint[PlaneBase, PlaneNorm, P3];

APPENDIX A

```
    ½Sqrt[(AP−BP)·(AP−BP)]Sqrt[
        ((−AP+CP)·(−AP+CP)−((AP−BP)·(AP−BP)−(BP−CP)·(BP−CP)+(−AP+CP)·(−AP+CP))
2/
            (4 (AP−BP)·(AP−BP)))]];
(*Calculate the distance from one point in 3 space to a plane in 3 space*)
PtDistance=Compile[{{PlaneBase, _Real, 1}, {PlaneNorm, _Real, 1}, {P1, _Real, 1}},
    dpt=P1−PlaneNorm*((P1−PlaneBase)·PlaneNorm);
    Sqrt[(Part[dpt, 1]−Part[P1, 1])^2+
        (Part[dpt, 2]−Part[P1, 2])^2+(Part[dpt, 3]−Part[P1, 3])^2]];
(*Directed Distance is the distance from point P1
to the plane. It is positive if the point is on the same*)
(* side as the normal vector is pointing, negative otherwise,
the normal must be of unit length!*)
DirectedDist=Compile[{{PlaneBase, _Real, 1}, {PlaneNorm, _Real, 1}, {P1, _Real, 1}},
    Dot[(P1−PlaneBase), PlaneNorm]];
(*Calculate the distance between two points*)
Distance=Compile[{{P1, _Real, 1}, {P2, _Real, 1}},
    Sqrt[(Part[P1, 1]−Part[P2, 1])*(Part[P1, 1]−Part[P2, 1])+
        (Part[P1, 2]−Part[P2, 2])*(Part[P1, 2]−Part[P2, 2])+
        (Part[P1, 3]−Part [P2, 3])*(Part[P1, 3]−Part[P2, 3])]];
MakeNormal=
    Compile[{{Vec, _Real, 1}}, Size=Sqrt[Part[Vec, 1]^2+Part[Vec, 2]^2+Part[Vec,3]^2;
        {Part[Vec, 1]/Size, Part[Vec, 2]/Size, Part[Vec, 3]/Size}];
(*This function returns the point where the line defined by P1−
        P2 crosses the plane defined by PlaneBase & PlaneNorm*)
IntersectPlane=
    Compile[{{PlaneBase, _Real, 1}, {PlaneNorm, _Real, 1), (P1, _Real, 1), (P2, _Real, 1)},
        t=(Part[PlaneBase, 1]*Part[PlaneNorm, 1]+Part[PlaneBase, 2]*Part[PlaneNorm, 2]+
            Part[PlaneBase, 3]*Part[PlaneNorm, 3]−Part[PlaneNorm, 1]*Part[P1, 1]−
            Part[PlaneNorm, 2]*Part[P1, 2]−Part[PlaneNorm, 3]*Part[P1, 3])/
            (Part[PlaneNorm, 1]*(Part[P2, 1]−Part[P1, 1])+Part[PlaneNorm, 2]*
            (Part[P2, 2]−Part[P1, 2])+Part[PlaneNorm, 3]*(Part[P2, 3]−Part[P1, 3]));
    P1+t*(P2−P1)
];
(*Load the data file*)
    LoadFileName="c:\\temp\mathsine.stl";
    SK=Import[LoadFileName];
(*Define the best fit plane, and find a point on the plane, and its
normal*)
    NK=Table[PT1=Part[Part[Part[Part[SK, 1], i], 1], 1];
    PT2=Part[Part[Part[Part[SK, 1] , i], 1], 2]; PT3=
        Part[Part[Part[Part[SK, l], i], 1], 3]; {(Part{PT1, 1]+Part[PT2, 1]+Part[PT3, l])/3,
        (Part[PT1, 2]+Part[PT2, 2]+Part[PT3, 2])/3,
        (Part[PT1, 3]+Part[PT2, 3]+Part[PT3, 3])/3), {i, 1, Count[Part[SK, 1], Polygon_]}];
    PlaneA=Fit [NK, (1, x, y), {x, y}];
(*Determine the location of the plane that best fits the data set*)
(* determine the "base" point, and the normal vector to the plane*)
    Base={0, 0, PlaneA/·{x→0, y→0}};
    XVec={1, 0, PlaneA/·{x→1, y→0}};
    YVec={0, 1, PlaneA/·{x→0, y→1}};
    PVec=Xvec−Base;
    PlaneNorm=MakeNormal[Cross[XVec−Base, YVec−Base]];
    (*generate a list of the distance from
        the center of the triangles to the best fit plane*)
    AllDist=
        Table[DirectedDist[Base, PlaneNorm, Part[NK, i]], {i, 1, Count[Part[SK, 1], Polygon_]}];
    (*Enter Tldi. This is the uncompressed
        thickness measured by the Get Thickness macro*)
    Tldi=0.1;
    (*Enter Tu. Tu is the compressed
        thickness measured using a thickness gage at 0.05 psi*)
    Tu=0.1;
    ShiftUp=Max[AllDist]−(Tldi−Tu);
    (*Calculate the distance to shift the
        best fit plant to approximate the location of the cover*)
    CoverBase=Base+ShiftUp*PlaneNorm;
(*Now do the main loop. Go through each triangle in the file and
calculate relaevent parameters*)
    TriType={ };
    Timing[For=1; ProjectedArea=0; PerimeterTot=0; ContactAreaTot=0;
        VolumeTot=0; SAunderTot=0; PerimeterLines={ }; SurfAreaTot=0;; Avx=0;
        Avy=0; Avz=0; VertArea=0; clx=100; cly=100; clz=100; D1=1000; c2x=100;
        c2y=100; c2z=100; D2=1000; c3x=100; c3y=100; c3z=100; D3=1000;
        c4x=100; c4y=100; c4z=100; D4=1000, i<Count[Part[SK, 1], Polygon_], i++,
(*Get the verticies for the triangle being analyzed*)
    P1=Part [Part[Part[Part[SK, 1], i], 1], l];
    P2=Part [Part[Part[Part[SK, 1], i], 1], 2];
    P3=Part [Part[Part[Part[SK, 1], i], 1], 3];
```

APPENDIX A

```
(*Calculate the average/center of the triangle *)
Avx=Avx+Part[P1, 1];
Avy=Avy+Part[P1, 2];
Avz=Avz+Part[P1, 3];
(*Generate a triangle that is projected onto the cover plane*)
k1=ProjectPoint[CoverBase, PlaneNorm, P1];
k2=ProjectPoint[CoverBase, PlaneNorm, P2];
k3=ProjectPoint[CoverBase, PlaneNorm, P3];
(*measure the distance from each vertice to the cover plane.*)
h1=DirectedDist[CoverBase, PlaneNorm, P1];
h2=DirectedDist[CoverBase, PlaneNorm, P2];
h3=DirectedDist[CoverBase, PlaneNorm, P3];
(*orient the points in order of distance from the
   plane. The analysis needs to have the verticies in decending order*)
If[(h1≥h2) && (h2≥h3), MaxPt=P1; kmax=k1; MidPt=P2; kmed=k2;
   LowPt=P3; kmin=k3; hmax=h1; hmid=h2; hmin=h3];
If[(h1≥h3) && (h3≥h2), MaxPt=P1; kmax=k1; MidPt=P3; kmed=k3;
   LowPt=P2; kmin=k2; hmax=h1; hmid=h3; hmin=h2];
If[(h2≥h1) && (h1≥h3), MaxPt=P2; kmax=k2; MidPt=P1; kmed=k1;
   LowPt=P3; kmin=k3; hmax=h2; hmid=h1; hmin=h3];
If[(h2≥h3) && (h3≥h1), MaxPt=P2; kmax=k2; MidPt=P3; kmed=k3;
   LowPt=P1; kmin=k1; hmax=h2; hmid=h3; hmin=h1];
If[(h3≥h1) && (h1≥h2), MaxPt=P3; kmax=k3; MidPt=P1; kmed=k1;
   LowPt=P2; kmin=k2; hmax=h3; hmid=h1; hmin=h2];
If[(h3≥h2) && (h2≥h1) , MaxPt=P3; kmax=k3; MidPt=P2; kmed=k2;
   LowPt=P1; kmin=k1; hmax=h3; hmid=h2; hmin=h1];
(*calculate and record the surface area of the triangle, and the projected area*)
SurfAreaTot=SurfAreaTot+SurfaceArea[P1, P2, P3];
ProjectedArea=ProjectedArea+SurfaceArea[k1, k2, k3;
(*Calculate the normal to the triangle,
   and use it to calculate the vertical component of the surface area*)
TriNorm=MakeNormal[Cross[(P2-P1), (P3-P1)]];
CA=Cross[TriNorm, PlaneNorm];
VertArea=VertArea+
   SurfaceArea[P1, P2, P3]*Sqrt[Part[CA, 1]^2[Part[CA, 2]^2+Part[CA, 3]^2];
(*do the following when all three points are below the plane*)
(*such a triangle does not contribute to the perimeter or the contact area*)
If[Sign[h1]≤0 && Sign[h2]≤ && Sign[h3]<0,
AppendTo[TriType, 3];
SAunderTot=SAunderTot+SurfaceArea[P1, P2, P3];
(*now calculate the volume in two parts. The first is a right triangular prism*)
V1=Abs[hmax]*SurfaceArea[kmin, kmed, kmax];
(*find the height of the pyramid defined by maxpt as apex,
   and P4, P5,midpt,minpt as base*)
(*if the triangle is on the plane then the volume is zero so set h=0*)
   If[kmed≠kmin && LowPt≠kmin,
   NewNorm=MakeNormal[Cross[(kmed-kmin), (LowPt-kmin)]];
   P4=ProjectPoint[kmed, NewNorm, MaxPt];
   h=Distance[P4, MaxPt];, h=0
];
(*Now calculate the area of the base of this pyramid*)
Area2=Distance[kmed, kmin]*((hmid-hmax)+(hmid-hmin)/2);
VolumeTot=VolumeTot+V1+h*Area2/3;
,
(*the triangle wasn't of type 3, check to see if it is type 1, 2, or 4*)
(*Do the following when there is
     one of the verticies above the plane, and two below it*)
  If[Sign[hmax]>0 && Sign[hmin]≤0 && Sign[hmid]≤0,
     AppendTo[TriType, 1];
     (*The I1-I2 segment is the intersection of the triangle with the plane*)
     I1=IntersectPlane[CoverBase, PlaneNorm, MaxPt, MidPt];
     I2=IntersectPlane[CoverBase, PlaneNorm, MaxPt, LowPt];
     (*Calculate the 'contact area' and the 'surface area' parts*)
     ContactArea=ContactArea+SurfaceArea[I1, I2, kmax];
     SAunderTot=SAunderTot+SurfaceArea[I1, I2, MidPt]+SurfaceArea[I2, MidPt, LowPt];
     PerimeterTot=PerimeterTot+Distance[I1, I2];
     AppendTo[PerimeterLines, Line[{I1, I2}]];
     Area2=SurfaceArea{I1, kmed, I2];
     Area3=Distance[kmed, kmin]*(Abs[hmid]+(hmid-hmin)/2);
     V1=Abs[hmid]*Area2/3;
     (*Now to calculate the height of the final volume pyramid,
     we must calculate the projection of I2 *)
     (* onto the plane defined by kmed,kmin and p3*)
     If[(LowPt≠kmin) &&( kmed≠kmin),
        NewNorm=MakeNormal[Cross[(kmed-kmin), (LowPt-kmin)]];
        P4=ProjectPoint[kmin, NewNorm, I2];
        h=Distance[P4, I2];
        V2=Area3*h/3;, V2=0;
```

-continued

APPENDIX A

```
    ];
    VolumeTot=VolumeTot+V1+V2;
    (*Do the following when two points are above the plane, and one below*)
    If[Sign[hmax]>0 && Sign[hmid]≥0 && Sign[hmin]<0,
        AppendTo[TriType, 2];
        (*The I1-I2 segment is the intersection of the triangle with the plane*)
        I2=IntersectPlane[CoverBase, PlaneNorm, MaxPt, LowPt];
        I1=IntersectPlane[CoverBase, PlaneNorm, MidPt, LowPt];
        PerimeterTot=PerimeterTot +Distance [I1, I2];
        AppendTo[PerimeterLines, Line[{I1, I2}]];
        SAunderTot=SAunderTot + SurfaceArea{I1, I2, LowPt];
        Area2=SurfaceArea[I1, I2, kmin];
        VolumeTot=VolumeTot,+Abs[hmin]+Area2/3;
        ContactAreaTot=
            ContactAreaTot+SurfaceArea[I1, I2, kmax] + SurfaceArea[kmax, kmed, I1];
        ,
        (*do the following if all three points are above the plane*)
        (*These do not contribute to volume, perimeter, or SAunderTot*)
        If[Sign[h1]≥0 && Sign[h2]≥ && Sign[h3]≥0,
            AppendTo[TriType, 4];
            ContactAreaTot=ContactAreaTot+SurfaceArea[kmed, kmin, kmax];
            ];
        ];
    ];
  ];
]]
(*Show the results from the analysis*)
LoadFileName
Tldi
Tu
Count[Part[SK, 1], Polygon_]
SurfAreaTot
VolumeTot
ProjectedArea
ContactAreaTot
PerimeterTot
VertArea
```

APPENDIX B

```
■ (*Load the function libraries *)
    <<Graphics`Graphics`
    <<Statistics`DescriptiveStatistics`
■ (*Define New Functions*)
    (*This is the function that determines
      the area of a triangle defined by points AB,BP,CP*)
    SurfaceArea=Compile[{{AP, _Real, 1}, {BP, _Real, 1}, {CP, _Real, 1}},
        If[(AP≠BP) && (AP≠CP) && (BP≠CP), ½Sqrt[(AP–BP)·(AP–BP)] Sqrt[
            ((–AP+CP)·(–AP+CP)–((AP–BP)·(AP–BP)–(BP–CP)·(BP–CP)+(–AP+CP)·(–AP+CP))²
            (4 (AP–BP)·(AP–BP)))], 0]];
    (*This is the function that defines the location
      of the point projected from P1 to the plane defined*)
    (* by the base point PlaneBase and the normal vector PlaneNorm. This
      projects the point along the normal onto the plane*)
    ProjectPoint=Compile[{{PlaneBase, _Real, 1}, {PlaneNorm, _Real, 1}, {P1, _Real, 1}},
        P1–PlaneNorm*((P1–PlaneBase)·PlaneNorm)];
    (*This function determines where a line defined by a point=
      InPoint and a direction vector=InVec *)
    (*intersects the plane defined by PlaneBase, and PlaneNorm*)
    PierceWhere=Compile[{{PlaneBase, _Real, 1},
        {PlaneNorm, _Real, 1), {InPoint, _Real, 1}, {InVec, _Real, 1}},
        t=(Dot[PlaneBase, PlaneNorm] –Dot[InPoint, PlaneNorm])/Dot[InVec, PlaneNorm];
        InPoint+t*InVec
    ];
    (*This function defines the area of a "Shadow" of a triangle projected onto a plane*)
    ProjectedArea=Compile[{{PlaneBase, _Real, 1}, {PlaneNorm, _Real, 1}, {P1, _Real, 1}
        {P2, _Real, 1}, {P3, _Real, 1}}, AP=ProjectPoint[PlaneBase, PlaneNorm, P1];
        BP=ProjectPoint[PlaneBase, PlaneNorm, P2];
        CP=ProjectPoint[PlaneBase, PlaneNorm, P3];
        ½Sqrt[(AP–BP)·(AP–BP)]Sqrt[
            ((–AP+CP)·(–AP+CP)–((AP–BP)·(AP–BP)–(BP–CP)·(BP–CP)+(–AP+CP)·(–AP+CP))²/
            (4 (AP–BP)·(AP–BP)))]];
    (*Calculate the distance from one point in 3 space to a plane in 3 space*)
```

APPENDIX B

```
PtDistance=Compile[{{PlaneBase, _Real, 1}, {PlaneNorm, _Real, 1}, {P1, _Real, 1}},
    dpt=P1-PlaneNorm*((P1-PlaneBase)·PlaneNorm);
    Sqrt[(Part[dpt, 1]-Part[P1, 1])^2+
        (Part[dpt, 2]-Part[P1, 2])^2+(Part[dpt, 3]-Part[P1, 3])^2]];
(*Directed Distance is the distance from point P1
    to the plane. It is positive if the point is on the same*)
(* side as the normal vector is pointing, negative otherwise,
    the normal must be of unit length!*)
DirectedDist=Compile[{{PlaneBase, _Real, 1}, {PlaneNorm, _Real, 1}, {P1, _Real, 1}},
    Dot[(P1-PlaneBase), PlaneNorm]];
(*Calculate the distance between two points*)
Distance=Compile[{{P1, _Real, 1), {P2, _Real, 1}},
    Sqrt[(Part[P1, 1]-Part[P2, 1])*(Part[P1, 1]-Part[P2, l])+
        (Part[P1, 2]-Part[P2, 2])*(Part[P1, 2]-Part[P2, 2])+
        (Part[P1, 3]-Part[P2, 3])*(Part[P1, 3]-Part[P2, 3])]];
(*Generate a normal vector that is in the direction of Vec *)
MakeNormal=Compile[{{Vec, _Real, l}},
    If[Not[Part[Vec, 1]==0 && Part[Vec, 2]==0 && Part[Vec, 3]==0],
        Size=Sqrt[Part[Vec, 1]^2+Part[Vec, 2]^2+Part [Vec, 3]^2], Size=-1];
    If[Size≠-1, {Part [Vec, 1]/Size, Part[Vec, 2]/Size, Part[Vec, 3]/Size}, Vec]
    ];
(*This function returns the point where the line defined by P1-
    P2 crosses the plane defined by PlaneBase & PlaneNorm*)
IntersectPlane=
    Compile[{{PlaneBase, _Real, 1}, {PlaneNorm, _Real, 1}, {P1, _Real, 1}, {P2, _Real, 1}},
        t=(Part[PlaneBase, l]*Part[PlaneNorm, l]+Part[PlaneBase, 2]*Part[PlaneNorm, 2]+
            Part[PlaneBase, 3]*Part[PlaneNorm, 3]-Part[PlaneNorm, 1]*Part [P1, 1]-
            Part[PlaneNorm, 2]*Part[P1, 2]-Part[PlaneNorm, 3]*Part[P1, 3])/
        (Part[PlaneNorm, 1]*(Part[P2, l]-Part[P1, 1])+Part[PlaneNorm, 2]*
        (Part[P2, 2]-Part[P1, 2])+Part[PlaneNorm, 3]*(Part[P2, 3]-Part[P1, 3]));
    P1+t*(P2-P1)
    ];
(*This function determines if the point QuPt is inside
    and on a triangle defined by P1,P2,P3, returns true or false*)
IsInside=Compile[{{P1, _Real, 1), {P2, _Real, 1}, {P3, _Real, 1}, {QuPt, _Real, 1}},
    delta=0.00000000001;
    AV={(Part[P1, 1]+Part[P2, 1]+Part[P3, 1])/3,
        (Part[P1, 2]+Part[P2, 2]+Part[P3, 2])/3,
        (Part[P1, 3]+Part[P2, 3]+Part[P3, 3])/3);
    If [Chop[MakeNormal[Cross[(QuPt-P1), (P2-P1)]]-MakeNormal[Cross[(AV-P1),(P2-P1)]]
        delta]=={0, 0, 0} && Chop[MakeNormal[Cross[(QuPt-P2), (P3-P2)]]-
            MakeNormal[Cross[(AV-P2), (P3-P2)]], delta]={0, 0, 0} &&
        Chop[MakeNormal[Cross[(QuPt-P3), (P1-P3)]]-MakeNormal[
            Cross[(AV-P3), (P1-P3)]], delta]={0, 0, 0}, 3=3, 4=3]
    ];
■ (*Load the data file*)
    FileN="C:\\temp\wavechunk.stl"
    C:\temp\wavechunk.stl
    SK=Import[FileN]
    -Graphics3D-
■ (*Define the best fit plane, and find a point on the plane, and its normal*)
    AveragePoints=Table[PT1=Part[Part[Part[Part[SK, 1], i], l], 1];
        PT2=Part[Part[Part[Part[SK, 1], i], 1], 2]; PT3=
            Part[Part[Part[Part[SK, 1], i], 1], 3]; {(Part[PT1, 1]+ Part[PT2, 1]+ Part[PT3, 1])/3,
            (Part[PTl, 2]+Part[PT2, 2]+Part[PT3, 2])/3,
            (Part[PT1, 3]+Part[PT2, 3]+Part[PT3, 3])/3}, {i, l, Count[Part[SK, l], Polygon_]}];
    PlaneA=Fit[AveragePoints, {1, x, y}, {x, y}];
(*Determine the location of the plane that best fits the data set*)
(* determine the "base" point, and the normal vector to the plane*)
Base={0, 0, PlaneA/·{x→0, y→0}};
XVec={1, 0, PlaneA/·{x→1, y→0}};
YVec={0, 1, Plane/·{x→0, y→1}};
PVec=XVec-Base;
PlaneNorm=MakeNormal[Cross[XVec-Base,YVec-Base]];
(*Split up the triangles into those
    that are on the top and those that are on the bottom*)
CRProduct=Table[Vec=MakeNormal[Cross[
        (Part[Part[Part[Part[SK, 1], i], l], 2] - Part[Part[Part[Part[SK, l], i], 1],l]),
        (Part[Part[Part[Part[SK, 1], i+, 1], 3]-Part[Part[Part[Part[SK, 1], i+, 1],1])]];
    CV=Dot[Vec, PlaneNorm], {i, 1, Count[Part[SK, l], Polygon_]}];
(*Now split the triangles into top and bottom
    sets based on their dot product with the plane normal*)
For[i=0; BottomTri={ }; TopTri={ }, i<Count[CRProduct, _Real], i++
    If[Part[CRProduct, i]<0,
        AppendTo[BottomTri, Part[Part[SK, 1], i]], AppendTo[TopTri, Part[Part[SK, 1], i]]];
    ];
BottomTri=graphics3D[BottomTri];
TopTri=Graphics3D[TopTri];
```

-continued

APPENDIX B

■ (*Determine the location of the Cover Plane and the Absorbent Plane*)
  (*The cover plane should be set by finding the highest point,
    and subtracting the difference between the uncompressed thickness*)
  (* and the thickness measured at 0.1 psi*)
  (*generate a list of the distance from
    the center of the triangles to the best fit Plane*)
  AverageTops=Table[PT1=Part[Part[Part[Part[TopTri, 1], i], 1], 1];
    PT2=Part[Part[Part[Part[TopTri, 1], i], 1], 2];
    PT3=Part[Part[Part[Part[TopTri, 1], i], 1], 3];
    {(Part[PT1, 1]+Part[PT2, 1]+Part[PT3, 1])/3,
      (Part[PT1, 2]+Part[PT2, 2]+Part[PT3, 2])/3,
      (Part[PT1, 3]+Part[PT2, 3]+Part[PT3, 3])/3},
    {i, 1, Count[Part[TopTri, 1], Polygon_]}];
  TopDist=Table[DirectedDist[Base, PlaneNorm, Part[AverageTops, i]],
    {i, 1, Count[Part[TopTri, 1], Polygon_]}];
  AverageBottoms=Table[PT1=Part[Part[Part[Part[BottomTri, 1], i], 1], 1];
    PT2=Part[Part[Part[Part[BottomTri, 1], i], 1], 2];
    PT3=Part[Part[Part[Part[BottomTri, 1], i], 1], 3];
    {(Part[PT1, 1]+Part[PT2, 1]+Part[PT3, 1])/3,
      (Part[PT1, 2]+Part[PT2, 2]+Part[PT3, 2])/3,
      (Part[PT1, 3]+Part[PT2, 3]+Part[PT3, 3])/3},
    {i, 1, Count[Part[BottomTri, l], Polygon_]}];
  BottomDist=Table[DirectedDist[Base, PlaneNorm, Part[AverageBottoms, i]],
    {i, 1, Count[Part[BottomTri, l], Polygon_]}];
  (*What is the distance where 10% of the TopDist
    values are greater? Set the top plane to that location*)
  ShiftUp=Part[Sort[TopDist}, IntegerPart[0.9*Count[TopDist, _Real]]];
  (*What is the distance where 10% of the BottomDist
    values are less? Set the bottom plane to that location*)
  ShiftDown=Part[Sort[BottomDist], IntegerPart[0.1*Count[BottomDist, _Real]]];
  (*These are the distances that the plane must
    be moved to approximate the location of the cover & absorbent*)
  CoverBase=Base+ShiftUp*PlaneNorm;
  (*Display the image with the plane*)
  AbsBase=Base+ShiftDown*PlaneNorm;
  CoverPlane=
    (Part[CoverBase, 3]*Part[PlaneNorm, 3]−Part[PlaneNorm, 1]*(x−Part[CoverBase, 1])−
      Part[PlaneNorm, 2]*(y−Part[CoverBase, 2]))/Part[PlaneNorm, 3];
  AbsPlane=
    (Part[AbsBase, 3]*Part[PlaneNorm, 3]−Part[PlaneNorm, 1]*(x−Part[AbsBase, 1])−
      Part[PlaneNorm, 2]*(y−Part[AbsBase, 2]))/Part[PlaneNorm, 3];
■ (*Go through each triangle in the bottom surface and find out if
there are any triangles that are above*)
(*the cover that have a center that is directly above the triangle.
*)
  (*make a table of triangle midpoints that are above the cover*)
  For[i=1; TopMidPoints={ }, i≤Count[AverageTops, Real_], i++,
    If [DirectDist[CoverBase, PlaneNorm, Part[AverageTops, i]] > 0,
      AppendTo[TopMidPoints, Point[Part[AverageTops, i]]]
    ];
  (*Now take a randomly chosen subset of 100 points,
    and use them to measure the thickness*)
  If[Count[TopMidPoints, Points_]>100,
    Pick=Take[Ordering[Table[Random[ ], {j, 1, Count[TopMidPoints, Points_]}]], 100];
    For[k=1; PickTopPoints={ }, k≤100, k++,
      AppendTo[PickTopPoints, Part[TopMidPoints, Part[Pick, k]]]];
    TopMidPoints=PickTopPoints;
  ];
  (*Now go through each triangle in the bottom surface,
  and find out if there is a corresponding average point
    that is directly above that triangle that is on the top
    surface. Directly above is in the PlaneNorm direction*)
  Timing[For[i=1; BThicks={ }; ThisTri={ }, i≤Count [Part[TopTri, l], Polygon_], i++,
    TP1=Part[Part[Part[Part[TopTri, l], i], 1], 1];
    TP2=Part[Part[Part[Part[TopTri, l], i], 1], 2];
    TP3=Part[Part[Part+part+BottomTri, l], i], 1], 3];
    TNorm=MakeNormal[Cross[(TP2−TP1), (TP3−TP1)]];
    ProjectedPoints=Table[PierceWhere[TP3, Norm,
      Part[Part[TopMidPoints, j], 1], PlaneNorm], {j, 1, Count[TopMidPoints, Points_]}];
    IsIn=Table[IsInside[TP1, TP2, TP3, Part[ProjectedPoints, j]],
      {j, 1, Count[TopMidPoints, Points_]}];
    ThisTri=Position[IsIn, True];
    If[Length[ThisTri]≠0,
      AppendTo[Thicks, Sqrt[(Part[Part[AverageBottoms, i], 1]−Part[
          Part[Part[Part[TopMidPoints, Part[ThisTri, 1]], 1], l], 1])^2+
        (Part[Part[AverageBottoms, i], 2]−Part[Part[Part[TopMidPoints,
          Part[ThisTri, 1]], 1], 1], 2])^2](Part[Part[AverageBottoms, i], 3]−
        Part[Part[Part[Part[TopMidPoints, Part[ThisTri, l]], 1], 1], 3]) ^ 2]]];

APPENDIX B

```
];]
(*Now determine the thickness of the bottom samples*)
(*Make a table of the triangle midpoints in the bottom surface*)
(*Generate a list of those triangle midpoints
   in the bottom surface that are below the Absorbent Plane*)
For[i=1; BotMidPoints={ }, i≤Count [AverageBottoms, Real_], i++,
   If[DirectDist[AbsBase, PlaneNorm, Part[AverageBottoms, i]]<=0,
      AppendTo[BotMidPoints, Point[Part[AverageBottoms, i]]]]
      ];
(*Now take a randomly chosen subset of 100 points,
and use them to measure the thickness*)
If[Count[BotMidPoints, Points_]>100,
   Pick=Take[Ordering[Table[Random[ ], {j, l, Count[BotMidPoints, Points_]}]], 100];
   For[k=1; PickBotPoints={ }, k≤100, k++,
      AppendTo[PickBotPoints, Part[BotMidPoints, Part[Pick, k]]]];
   BotMidPoints=PickBotPoints;
   ];
(*Now go through each triangle in the top surface,
and find out if there is a corresponding average point
   that is directly below that triangle on the bottom
   surface. Directly below is in the PlaneNorm direction*)
Timing[For[i=l; BThicks={ }; ThisTri={ }, i≤Count[Part[TopTri, 1], Polygon_], i++,
   TP1=Part [Part [Part [Part[TopTri, 1], i], 1], 1];
   TP2=Part [Part [Part [Part[TopTri, 1], i], 1], 2];
   TP3=Part [Part [Part [Part[TopTri, 1], i], 1], 3];
   TNorm=MakeNormal [Cross [(TP2-TP1), (TP3-TP1)]];
   ProjectedPoints=Table[PierceWhere [TP3, TNorm,
      Part[Part[BotMidPoints, j, 1], PlaneNorm], {j, 1, Count[BotMidPoints, Points_]}];
   IsIn=Table[IsInside[TP1, TP2, TP3, Part [ProjectedPoints, j]],
      {j, 1, Count[BotMidPoints, Points_]}];
   ThisTri=Position[IsIn, True];
   If [Length[ThisTri]≠0, AppendTo[BThicks, Sqrt[(Part[Part[AverageTops, i], 1]-
             Part[Part[Part[Part[BotMidPoints, Part[ThisTri, 1]], 1], 1], 1])^2+
         (Part[Part[AverageTops, i], 2]-Part[Part[Part[Part[BotMidPoints,
             Part[ThisTri, 1]], 1], 1], 2])^2+(Part[Part[AverageTops, i], 3]-
             Part[Part[Part[Part[BotMidPoints, Part[ThisTri, 1]], 1], 1], 3])^2]]];
   ];]
Print[FileN]
(*Results measuring the thickness of the Tops of the bumps. Top is defined as the
   level where 10% of the triangles in the upper surface are above that height.*)
(*Now show the actual average of the thickness at the top of the material*)
Mean[Thicks//N]
StandardDeviation[Thicks//N]
(*Results measuring the thickness of the Bottom of the bumps. Bottom is defined as
   the level where 10% of the triangles in the lower surface are below that height. *)
(*Now show the actual average of the bottom thickness*)
Mean[BThicks//N]
StandardDeviation[BThicks//N]
```

What is claimed is:

1. A method of making an absorbent structure having a three-dimensional topography comprises:
   placing at least a portion of the absorbent structure between opposed mold surfaces, at least one of the mold surfaces having a three-dimensional topography; and
   imparting the three-dimensional topography of the mold surface onto the absorbent structure so that the absorbent structure has a three-dimensional topography corresponding to the three-dimensional topography of the mold surface, the absorbent structure having the three-dimensional topography imparted thereon having a projected area as determined by a Topography Analysis Method, an upper surface of the absorbent structure having a vertical area as determined by the Topography Analysis Method in the range of about 0.1 cm$^2$ to about 0.5 cm$^2$ per 1.0 cm$^2$ projected area of the absorbent structure.

2. The method of claim 1 wherein imparting the three-dimensional topography of the mold surface onto the absorbent structure comprises compressing the absorbent structure between the mold surfaces.

3. The method of claim 1 wherein imparting the three-dimensional topography of the mold surface onto the absorbent structure comprises passing the absorbent structure between a nip defined by two opposed rolls.

4. The method of claim 1 wherein each of the mold surfaces has a three-dimensional topography to impart a three-dimensional topography on both upper and lower surfaces of the absorbent structure.

5. The method of claim 1 wherein the opposed mold surfaces comprise a first mold surface having a plurality of bumps and a second mold surface having a plurality of depressions, each of the depressions in the second mold surface being suitably sized and shaped to receive a respective one of the bumps of the first mold surface.

6. The method of claim 1 further comprising forming the absorbent structure from absorbent fibers and a binder material using an airlaying technique.

7. The method of claim 6 wherein the binder material is heat activatable binder material.

8. The method of claim 7 further comprising heating the absorbent structure to a temperature sufficient to activate the heat activatable binder material.

9. A method of making an absorbent structure having a three-dimensional topography comprises:

passing the absorbent structure through a nip defined by opposed rolls, at least one of the rolls having a mold surface with a three-dimensional topography; and imparting the three-dimensional topography of the mold surface onto the absorbent structure so that the absorbent structure has a three-dimensional topography corresponding to the three-dimensional topography of the mold surface, the absorbent structure having the three-dimensional topography imparted thereon having a projected area as determined by a Topography Analysis Method, an upper surface of the absorbent structure having a vertical area as determined by the Topography Analysis Method in the range of about 0.1 cm$^2$ to about 0.5 cm$^2$ per 1.0 cm$^2$ projected area of the absorbent structure.

10. The method of claim 9 wherein one of the opposed rolls comprise a first mold surface having a plurality of bumps and the other roll comprises a second mold surface having a plurality of depressions, each of the depressions in the second mold surface being suitably sized and shaped to receive a respective one of the bumps of the first mold surface.

11. The method of claim 10 wherein the plurality of depressions comprises a plurality of circular depressions and the plurality of bumps comprises a plurality of cross-shaped bumps.

12. The method of claim 9 wherein each of the rolls has a mold surface with a three-dimensional topography to impart a three-dimensional topography on both upper and lower surfaces of the absorbent structure.

13. The method of claim 9 further comprising forming the absorbent structure from absorbent fibers and a binder material using an airlaying technique.

14. The method of claim 13 wherein the binder material is heat activatable binder material.

15. The method of claim 14 further comprising heating the absorbent structure to a temperature sufficient to activate the heat activatable binder material.

\* \* \* \* \*